United States Patent
Feng et al.

(10) Patent No.: US 8,039,817 B2
(45) Date of Patent: Oct. 18, 2011

(54) COMPENSATOR FOR MULTIPLE SURFACE IMAGING

(75) Inventors: Wenyi Feng, San Diego, CA (US);
Jason Bryant, Essex (GB); Dale Buermann, Los Altos, CA (US)

(73) Assignee: Illumina, Inc., San Diego, CA (US)

( * ) Notice: Subject to any disclaimer, the term of this patent is extended or adjusted under 35 U.S.C. 154(b) by 372 days.

(21) Appl. No.: 12/434,495

(22) Filed: May 1, 2009

(65) Prior Publication Data
US 2009/0272914 A1 Nov. 5, 2009

Related U.S. Application Data

(60) Provisional application No. 61/050,522, filed on May 5, 2008, provisional application No. 61/138,444, filed on Dec. 17, 2008.

(51) Int. Cl.
*G01N 21/64* (2006.01)
(52) U.S. Cl. ............................... 250/459.1
(58) Field of Classification Search ............... 250/259.1, 250/458.1, 576
See application file for complete search history.

(56) References Cited

U.S. PATENT DOCUMENTS

| | | |
|---|---|---|
| 5,324,633 A | 6/1994 | Fodor et al. |
| 5,451,683 A | 9/1995 | Barrett et al. |
| 5,482,867 A | 1/1996 | Barrett et al. |
| 5,491,074 A | 2/1996 | Aldwin et al. |
| 5,599,675 A | 2/1997 | Brenner |
| 5,624,711 A | 4/1997 | Sundberg et al. |
| 5,646,411 A | 7/1997 | Kain et al. |
| 5,744,305 A | 4/1998 | Fodor et al. |
| 5,750,341 A | 5/1998 | Macevicz |
| 5,795,716 A | 8/1998 | Chee |
| 5,831,070 A | 11/1998 | Pease et al. |
| 5,856,101 A | 1/1999 | Hubbell et al. |
| 5,858,659 A | 1/1999 | Sapolsky et al. |

(Continued)

FOREIGN PATENT DOCUMENTS

DE 100 14 204 A1 10/2001

(Continued)

OTHER PUBLICATIONS

Grover et al., "Monolithic membrane valves and diaphragm pumps for practical large-scale integration into glass microfluid devices," Sensors and Actuators B 89:315-323 (2003).

(Continued)

*Primary Examiner* — Kiho Kim
(74) *Attorney, Agent, or Firm* — Fletcher Yoder, PC

(57) ABSTRACT

A system and method for imaging biological samples on multiple surfaces of a support structure are disclosed. The support structure may be a flow cell through which a reagent fluid is allowed to flow and interact with the biological samples. Excitation radiation from at least one radiation source may be used to excite the biological samples on multiple surfaces. In this manner, fluorescent emission radiation may be generated from the biological samples and subsequently captured and detected by detection optics and at least one detector. The detected fluorescent emission radiation may then be used to generate image data. This imaging of multiple surfaces may be accomplished either sequentially or simultaneously. In addition, the techniques of the present invention may be used with any type of imaging system. For instance, both epifluorescent and total internal reflection methods may benefit from the techniques of the present invention.

27 Claims, 18 Drawing Sheets

U.S. PATENT DOCUMENTS

| | | | |
|---|---|---|---|
| 5,874,219 A | 2/1999 | Rava et al. |
| 5,968,740 A | 10/1999 | Fodor et al. |
| 5,974,164 A | 10/1999 | Chee |
| 5,981,185 A | 11/1999 | Matson et al. |
| 5,981,956 A | 11/1999 | Stern |
| 6,022,963 A | 2/2000 | McGall et al. |
| 6,025,601 A | 2/2000 | Trulson et al. |
| 6,033,860 A | 3/2000 | Lockhart et al. |
| 6,083,697 A | 7/2000 | Beecher et al. |
| 6,090,555 A | 7/2000 | Fiekowsky et al. |
| 6,136,269 A | 10/2000 | Winkler et al. |
| 6,291,183 B1 | 9/2001 | Pirrung et al. |
| 6,309,831 B1 | 10/2001 | Goldberg et al. |
| 6,327,410 B1 | 12/2001 | Walt et al. |
| 6,355,431 B1 | 3/2002 | Chee et al. |
| 6,416,949 B1 | 7/2002 | Dower et al. |
| 6,428,752 B1 | 8/2002 | Montagu |
| 6,482,591 B2 | 11/2002 | Lockhart et al. |
| 6,770,441 B2 | 8/2004 | Dickinson et al. |
| 7,057,026 B2 | 6/2006 | Barnes et al. |
| 7,115,400 B1 | 10/2006 | Adessi et al. |
| 7,244,559 B2 | 7/2007 | Rothberg et al. |
| 7,329,860 B2 | 2/2008 | Feng et al. |
| 2002/0102578 A1 | 8/2002 | Dickinson et al. |
| 2003/0108900 A1 | 6/2003 | Oliphant et al. |
| 2003/0215821 A1 | 11/2003 | Gunderson et al. |
| 2004/0096831 A1 | 5/2004 | Hughes |
| 2004/0185483 A1 | 9/2004 | Stuelpnagel et al. |
| 2004/0248287 A1 | 12/2004 | Hu et al. |
| 2005/0057798 A1 | 3/2005 | Osborne et al. |
| 2005/0100900 A1 | 5/2005 | Kawashima et al. |
| 2005/0181394 A1 | 8/2005 | Steemers et al. |
| 2005/0191698 A1 | 9/2005 | Chee et al. |
| 2006/0188901 A1 | 8/2006 | Barnes et al. |
| 2006/0240439 A1 | 10/2006 | Smith et al. |
| 2006/0253035 A1 | 11/2006 | Stern |
| 2006/0281109 A1 | 12/2006 | Barr Ost et al. |
| 2007/0114362 A1 | 5/2007 | Feng et al. |
| 2007/0166705 A1 | 7/2007 | Milton et al. |
| 2008/0262747 A1 | 10/2008 | Kain et al. |
| 2008/0297911 A1 * | 12/2008 | Christenson et al. ......... 359/666 |
| 2009/0309049 A1 * | 12/2009 | Van Dijk et al. ........... 250/578.1 |

FOREIGN PATENT DOCUMENTS

| | | | |
|---|---|---|---|
| WO | 98/44151 A1 | 10/1998 |
| WO | 00/18957 A1 | 4/2000 |
| WO | 00/63437 A2 | 10/2000 |
| WO | 2005/065814 A1 | 7/2005 |
| WO | 2006/064199 A1 | 6/2006 |
| WO | 2007/010251 A2 | 1/2007 |
| WO | 2007/123744 A2 | 11/2007 |

OTHER PUBLICATIONS

Shendure et al.; "Accurate Multiplex Polony Sequencing of an Evolved Bacteria Genome," Science 309:1728-1732 (2005).

* cited by examiner

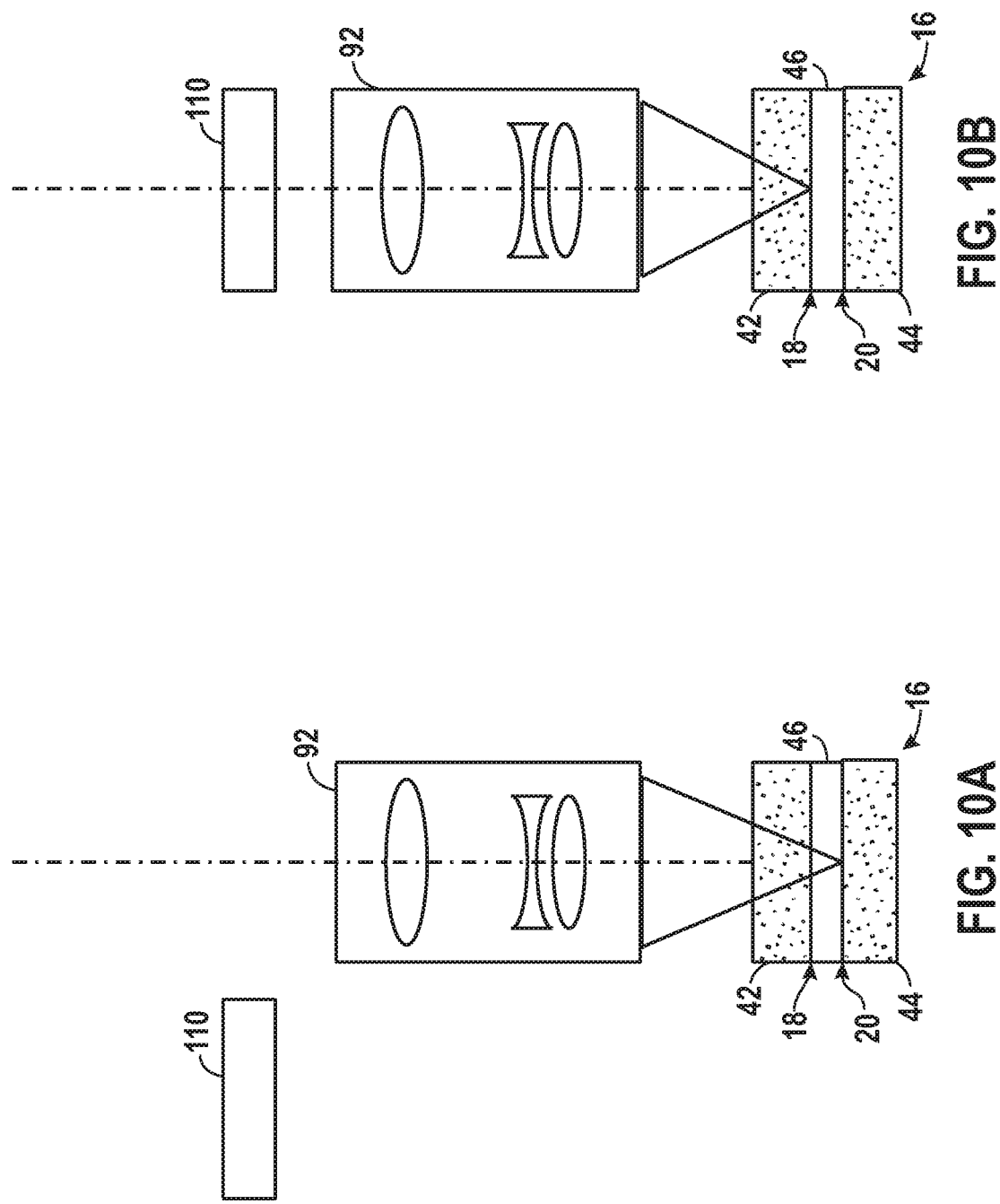

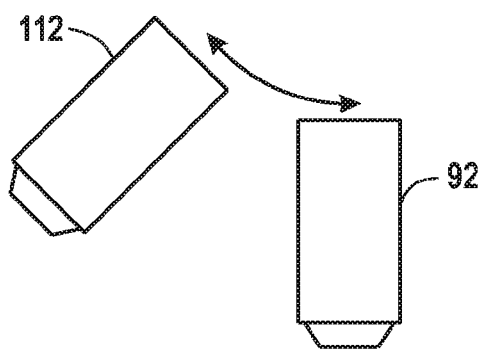
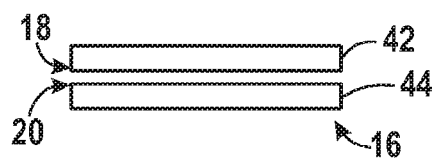
FIG. 11
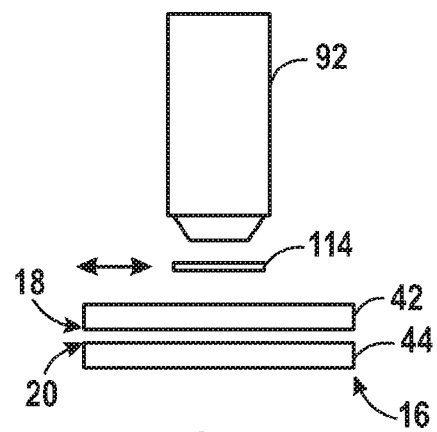
FIG. 12
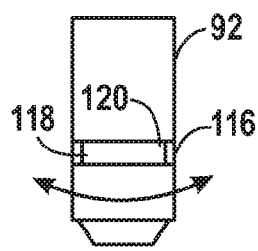
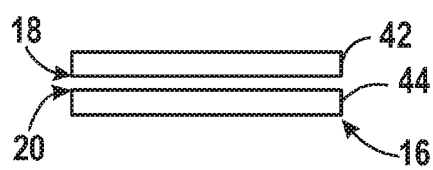
FIG. 13
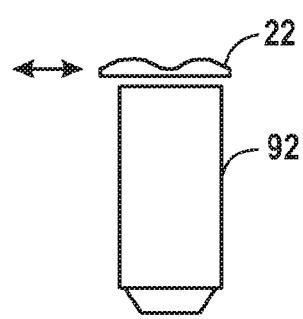
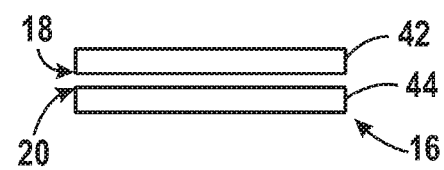
FIG. 14

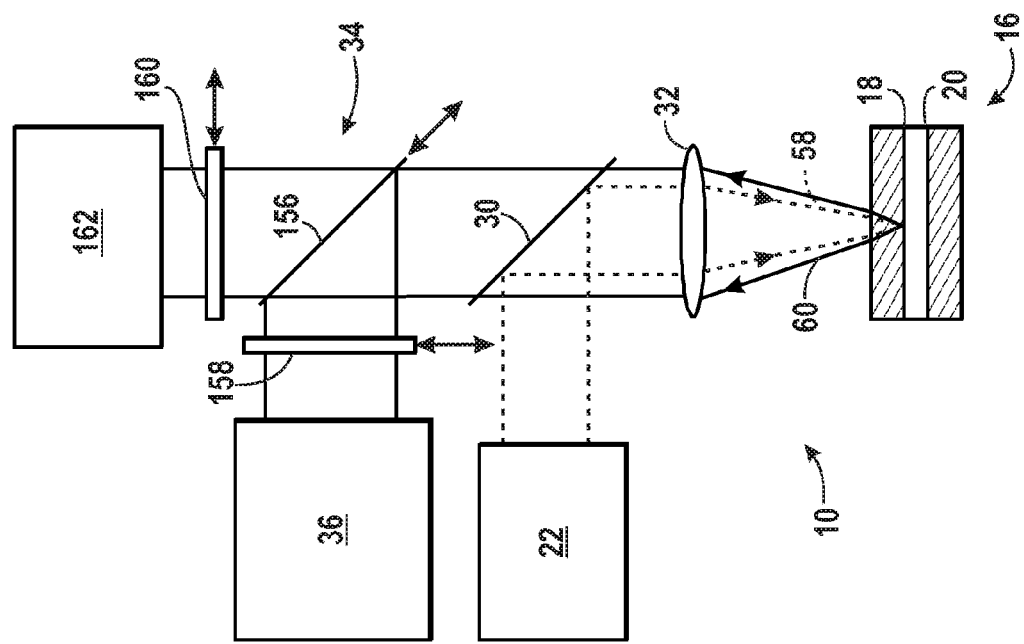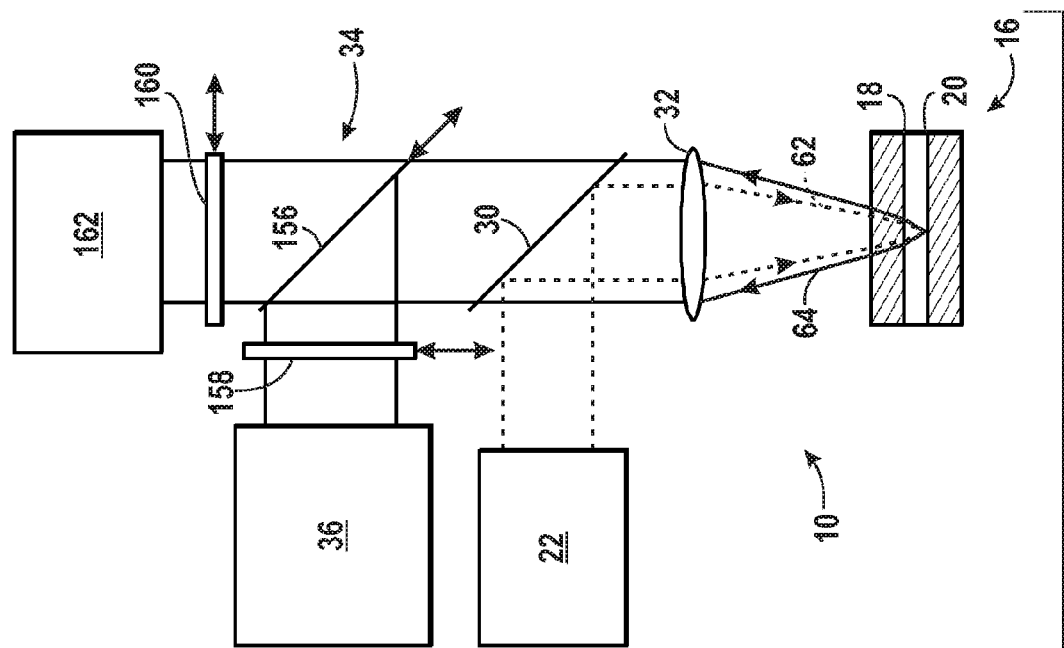
FIG. 18

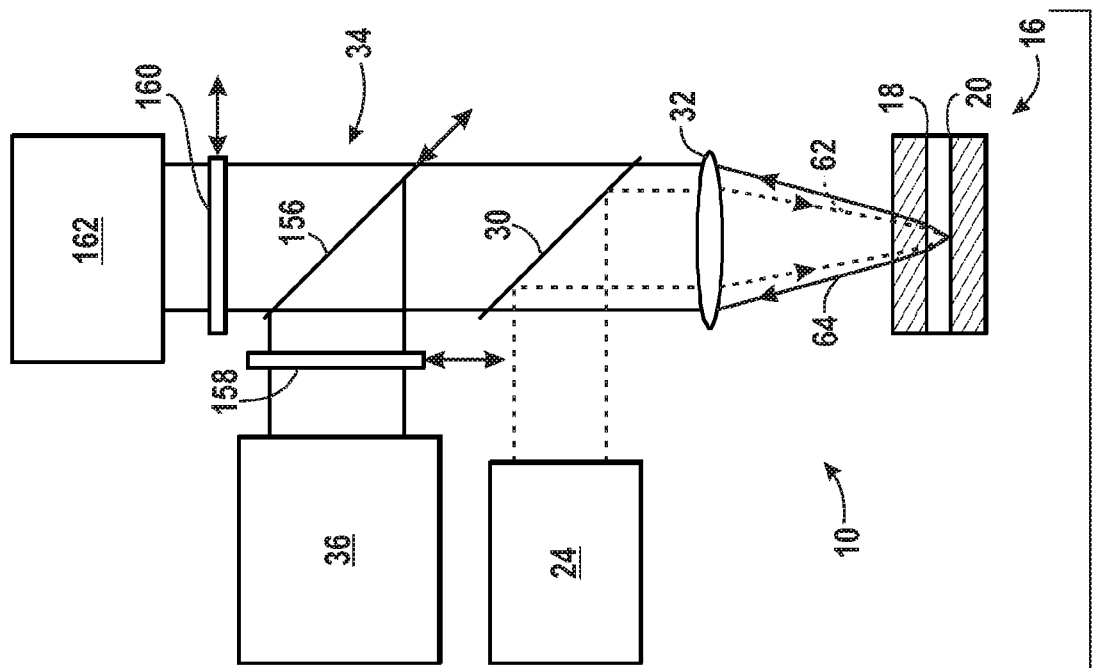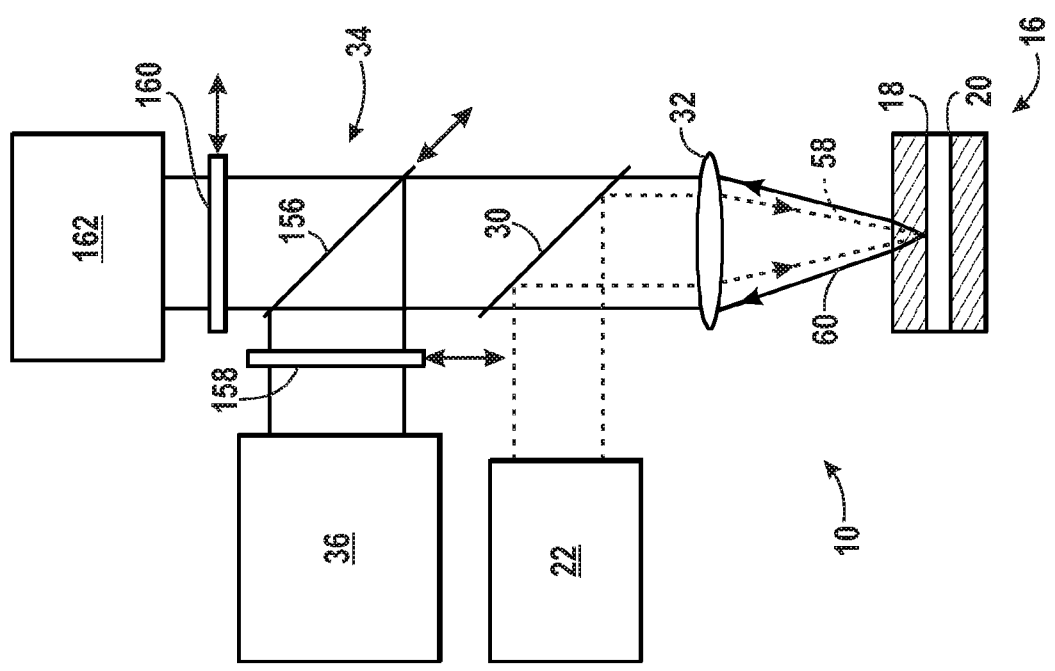
FIG. 19

COMPENSATOR FOR MULTIPLE SURFACE IMAGING

CROSS REFERENCE TO RELATED APPLICATIONS

This application claims priority of U.S. Provisional Patent Application No. 61/050,522, entitled "Multi-Surface Biological Sample Imaging System and Method," filed May 5, 2008, which is herein incorporated in its entirety by reference, and of U.S. Provisional Patent Application No. 61/138,444, entitled "Compensator for Multiple Surface Imaging," filed Dec. 17, 2008, which is herein incorporated in its entirety by reference.

BACKGROUND

The present invention relates generally to the field of imaging and evaluating analytical samples. More particularly, the invention relates to a technique for imaging and evaluating analytical samples on multiple surfaces of a support structure using a compensator.

There are an increasing number of applications for imaging of analytical samples on a support structure. These support structures may include plates upon which biological samples are present. For instance, these plates may include deoxyribonucleic acid (DNA) and ribonucleic acid (RNA) probes that are specific for nucleotide sequences present in genes in humans and other organisms. Individual DNA or RNA probes can be attached at specific locations in a small geometric grid or array on the support structure. Depending upon the technology employed, the samples may attach at random, semi-random or predetermined locations on the support structure. A test sample, such as from a known person or organism, can be exposed to the array or grid, such that complementary genes or fragments hybridize to probes at the individual sites on a surface of a plate. In certain applications, such as sequencing, templates or fragments of genetic material may be located at the sites, and nucleotides or other molecules may be caused to hybridize to the templates to determine the nature or sequence of the templates. The sites can then be examined by scanning specific frequencies of light over the sites to identify which genes or fragments in the sample were present, by fluorescence of the sites at which genes or fragments hybridized.

These plates are sometimes referred to as microarrays, gene or genome chips, DNA chips, gene arrays, and so forth, and may be used for expression profiling, monitoring expression levels, genotyping, sequencing, and so forth. For example, diagnostic uses may include evaluation of a particular patient's genetic makeup to determine whether a disease state is present or whether pre-disposition for a particular condition exists. The reading and evaluation of such plates are an important aspect of their utility. Although microarrays allow separate biological components to be presented for bulk processing and individual detection, the number of components that can be detected in a single experiment is limited by the resolution of the system. Furthermore, the bulk reagents used in some methods can be expensive such that reduced volumes are desired. The present invention provides methods and compositions that increase the efficiency of array based detection to counteract these limitations. Other advantages are provided as well and will be apparent from the description below.

BRIEF DESCRIPTION

The present invention provides a novel approach to analytical sample imaging and evaluation that expands the use of imaging and evaluation subsystems to multiple surfaces that support samples. The support structure may, for instance, be a flow cell through which a reagent fluid is allowed to flow and interact with biological samples. Excitation radiation from at least one radiation source may be used to excite the biological samples on multiple surfaces. In this manner, fluorescent radiation may be emitted from the biological samples and subsequently captured and detected by detection optics and at least one detector. The returned radiation may then be used to generate image data. This imaging of multiple surfaces may be accomplished either sequentially or simultaneously. In addition, the techniques of the present invention may be used with any of a variety of types of imaging systems. For instance, both epifluorescent and total internal reflection (TIR) methods may benefit from the techniques of the present invention. In addition, the biological samples imaged may be present on the surfaces of the support structure in random locations or in patterns.

Accordingly, the invention provides a method for imaging a biological sample. The method includes detecting radiation emitted from a first emissive component of a biological sample disposed on a first surface of a flow cell using a detector. The flow cell is mounted on an imaging station. The method also includes inserting corrective optics between the detector and the flow cell. The method further includes detecting radiation emitted from a second emissive component of a biological sample disposed on a second surface of the flow cell using the detector and the corrective optics. The first and second surfaces are in an arrangement whereby one of the surfaces is disposed between the detector and the other surface. In addition, the corrective optics reduce aberration of detection at one of the surfaces due to the arrangement. The steps of the method are repeated while maintaining the flow cell on the imaging station.

The invention further provides an imaging system for detecting radiation on a multi-surface flow cell. The imaging system includes a multi-surface flow cell having first and second emissive components of a biological sample disposed on respective first and second surfaces of the flow cell. The imaging system also includes an optical train including an objective, imaging optics configured to focus the optical train on the first emissive component via the objective, and corrective optics configured to focus the optical train on the second emissive component and configured to reduce aberration of detection at the first or second emissive component. The imaging system further includes a radiation source configured to direct excitation radiation towards the first and second emissive components. In addition, the imaging system includes detection optics configured to capture emitted radiation returned from the first and second emissive components via the optical train. Further, the imaging system includes a detector for detecting the captured radiation.

DRAWINGS

FIG. 10A illustrates an exemplary objective imaging the second surface without the assistance of a compensator in accordance with the present invention;

FIG. 10B illustrates an exemplary objective imaging the first surface with the assistance of a compensator in accordance with the present invention;

FIG. 11 is an exemplary compensator design, incorporating a first objective and a second objective which may replace the first objective in the optical train in accordance with the present invention;

FIG. 12 is another exemplary compensator design, incorporating a corrective device which may be inserted between the objective and the support structure in accordance with the present invention;

FIG. 13 is another exemplary compensator design, incorporating a correction collar in accordance with the present invention;

FIG. 14 is another exemplary compensator design, incorporating an infinite space compensator in accordance with the present invention;

FIG. 18 is a diagrammatical view of a biological sample imaging system with one radiation source and dual detectors configured to sequentially scan multiple surfaces of the support structure in accordance with the present invention;

FIG. 19 is a diagrammatical view of a biological sample imaging system with dual radiation sources and dual detectors configured to sequentially scan multiple surfaces of the support structure in accordance with the present invention;

DETAILED DESCRIPTION

Figure 1:
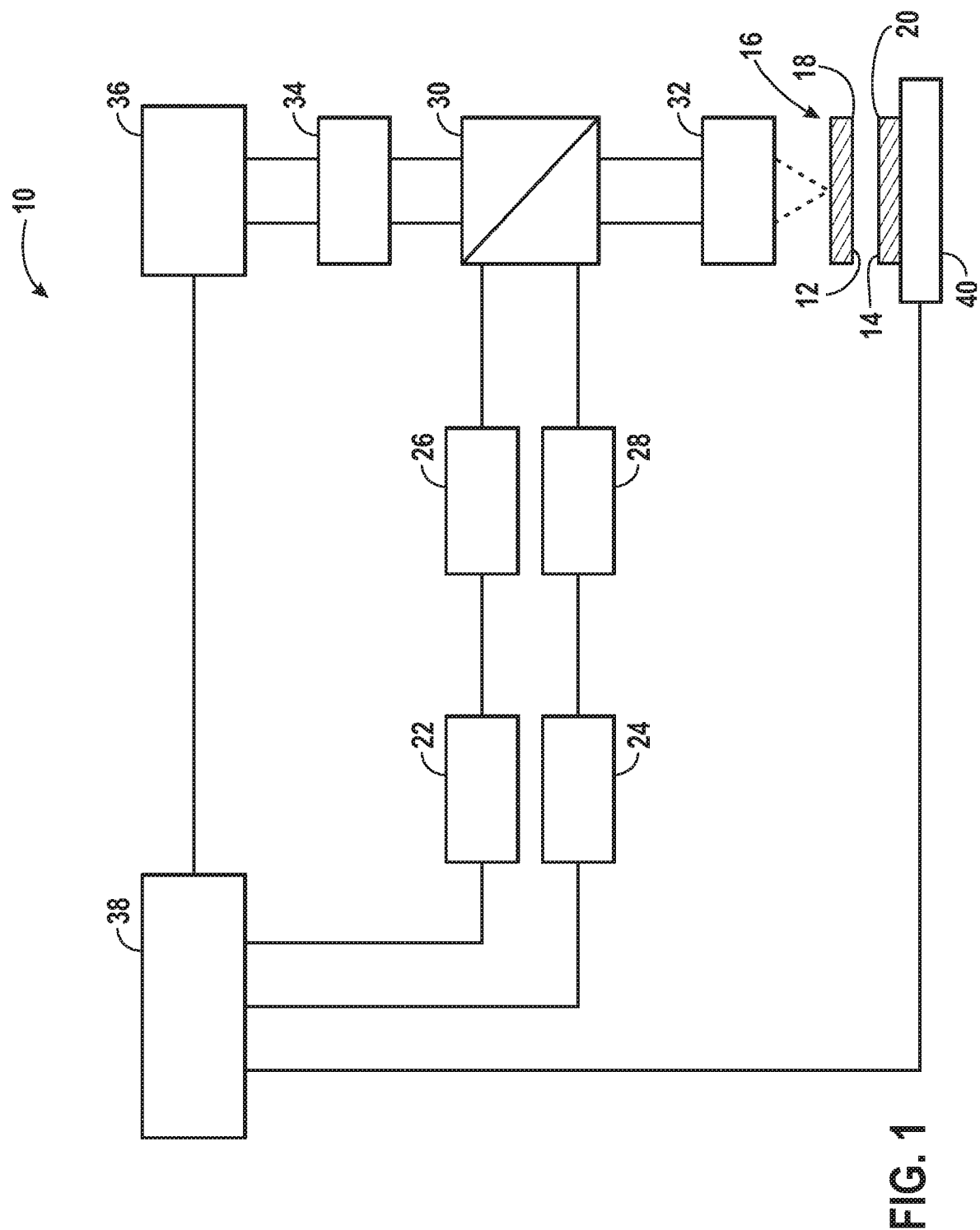
FIG. 1 is a diagrammatical overview for a biological sample imaging system in accordance with the present invention.

Turning now to the drawings, and referring first to FIG. 1, a biological sample imaging system 10 is illustrated diagrammatically. The biological sample imaging system 10 is capable of imaging multiple biological components 12, 14 within a support structure 16. For instance, in the illustrated embodiment, a first biological component 12 may be present on a first surface 18 of the support structure 16 while a second biological component 14 may be present on a second surface 20 of the support structure. The support structure 16 may, for instance, be a flow cell with an array of biological components 12, 14 on the interior surfaces 18, 20 which generally mutually face each other and through which reagents, flushes, and other fluids may be introduced, such as for binding nucleotides or other molecules to the sites of biological components 12, 14. The support structure 16 may be manufactured in conjunction with the present techniques or the support structure 16 may be purchased or otherwise obtained from a separate entity. Fluorescent tags on the molecules that bind to the components may, for instance, include dyes that fluoresce when excited by appropriate excitation radiation. Assay methods that include the use of fluorescent tags and that can be used in an apparatus or method set forth herein include those set forth elsewhere herein such as genotyping assays, gene expression analysis, methylation analysis, or nucleic acid sequencing analysis.

Those skilled in the art will recognize that a flow cell or other support structure may be used with any of a variety of arrays known in the art to achieve similar results. Furthermore, known methods for making arrays can be used, and if appropriate, modified in accordance with the teaching set forth herein in order to create a flow cell or other support structure having multiple surfaces useful in the detection methods set forth herein. Such arrays may be formed by disposing the biological components of samples randomly or in predefined patterns on the surfaces of the support by any known technique. In a particular embodiment, clustered arrays of nucleic acid colonies can be prepared as described in U.S. Pat. No. 7,115,400; U.S. Patent Application Publication No. 2005/0100900; PCT Publication No. WO 00/18957; or PCT Publication No. WO 98/44151, each of which is hereby incorporated by reference. Such methods are known as bridge amplification or solid-phase amplification and are particularly useful for sequencing applications.

Other exemplary random arrays, and methods for their construction, that can be used in the invention include, without limitation, those in which beads are associated with a solid support, examples of which are described in U.S. Pat. Nos. 6,355,431; 6,327,410; and 6,770,441; U.S. Patent Application Publication Nos. 2004/0185483 and US 2002/0102578; and PCT Publication No. WO 00/63437, each of which is hereby incorporated by reference. Beads can be located at discrete locations, such as wells, on a solid-phase support, whereby each location accommodates a single bead.

Any of a variety of other arrays known in the art or methods for fabricating such arrays can be used in the present invention. Commercially available microarrays that can be used include, for example, an Affymetrix® GeneChip® microarray or other microarray synthesized in accordance with techniques sometimes referred to as VLSIPS™ (Very Large Scale Immobilized Polymer Synthesis) technologies as described, for example, in U.S. Pat. Nos. 5,324,633; 5,744,305; 5,451,683; 5,482,867; 5,491,074; 5,624,711; 5,795,716; 5,831,070; 5,856,101; 5,858,659; 5,874,219; 5,968,740; 5,974,164; 5,981,185; 5,981,956; 6,025,601; 6,033,860; 6,090,555; 6,136,269; 6,022,963; 6,083,697; 6,291,183; 6,309,831; 6,416,949; 6,428,752; and 6,482,591, each of which is hereby incorporated by reference. A spotted microarray can also be used in a method of the invention. An exemplary spotted microarray is a CodeLink™ Array available from Amersham Biosciences. Another microarray that is useful in the invention is one that is manufactured using inkjet printing methods such as SurePrint™ Technology available from Agilent Technologies.

Sites or features of an array are typically discrete, being separated with spaces between each other. The size of the sites and/or spacing between the sites can vary such that arrays can be high density, medium density, or lower density. High density arrays are characterized as having sites separated by less than about 15 µm. Medium density arrays have sites separated by about 15 to 30 µm, while low density arrays have sites separated by greater than 30 µm. An array useful in the invention can have sites that are separated by less than 100 µm, 50 µm, 10 µm, 5 µm, 1 µm or 0.5 µm. An apparatus or method of the invention can be used to image an array at a resolution sufficient to distinguish sites at the above densities or density ranges.

As exemplified herein, a surface used in an apparatus or method of the invention is typically a manufactured surface. It is also possible to use a natural surface or a surface of a natural support structure; however the invention can be carried out in embodiments where the surface is not a natural material or a surface of a natural support structure. Accordingly, components of biological samples can be removed from their native environment and attached to a manufactured surface.

Any of a variety of biological components can be present on a surface for use in the invention. Exemplary components include, without limitation, nucleic acids such as DNA or RNA, proteins such as enzymes or receptors, polypeptides, nucleotides, amino acids, saccharides, cofactors, metabolites or derivatives of these natural components. Although the apparatus and methods of the invention are exemplified herein with respect to components of biological samples, it will be understood that other samples or components can be used as well. For example, synthetic samples can be used such as combinatorial libraries, or libraries of compounds having species known or suspected of having a desired structure or function. Thus, the apparatus or methods can be used to synthesize a collection of compounds and/or screen a collection of compounds for a desired structure or function.

Returning to the exemplary system of FIG. 1, the biological sample imaging system 10 may include at least a first radiation source 22 but may also include a second radiation source 24 (or additional sources). The radiation sources 22, 24 may be lasers operating at different wavelengths. The selection of the wavelengths for the lasers will typically depend upon the fluorescence properties of the dyes used to image the component sites. Multiple different wavelengths of the lasers used may permit differentiation of the dyes at the various sites within the support structure 16, and imaging may proceed by successive acquisition of a series of images to enable identification of the molecules at the component sites in accordance with image processing and reading logic generally known in the art. Other radiation sources known in the art can be used including, for example, an arc lamp or quartz halogen lamp. Particularly useful radiation sources are those that produce electromagnetic radiation in the ultraviolet (UV) range (about 200 to 390 nm), visible (VIS) range (about 390 to 770 nm), infrared (IR) range (about 0.77 to 25 microns), or other range of the electromagnetic spectrum.

For ease of description, embodiments utilizing fluorescence-based detection are used as examples. However, it will be understood that other detection methods can be used in connection with the apparatus and methods set forth herein. For example, a variety of different emission types can be detected such as fluorescence, luminescence, or chemiluminescence. Accordingly, components to be detected can be labeled with compounds or moieties that are fluorescent, luminescent, or chemiluminescent. Signals other than optical signals can also be detected from multiple surfaces using apparatus and methods that are analogous to those exemplified herein with the exception of being modified to accommodate the particular physical properties of the signal to be detected.

Output from the radiation sources 22, 24 may be directed through conditioning optics 26, 28 for filtering and shaping of the beams. For example, in a presently contemplated embodiment, the conditioning optics 26, 28 may generate a generally linear beam of radiation, and combine beams from multiple lasers, for example, as described in U.S. Pat. No. 7,329,860. The laser modules can additionally include a measuring component that records the power of each laser. The measurement of power may be used as a feedback mechanism to control the length of time an image is recorded in order to obtain uniform exposure, and therefore more readily comparable signals.

After passing through the conditioning optics 26, 28, the beams may be directed toward directing optics 30 which redirect the beams from the radiation sources 22, 24 toward focusing optics 32. The directing optics 30 may include a dichroic mirror configured to redirect the beams toward the focusing optics 32 while also allowing certain wavelengths of a retrobeam to pass therethrough. The focusing optics 32 may confocally direct radiation to one or more surfaces 18, 20 of the support structure 16 upon which individual biological components 12, 14 are located. For instance, the focusing optics 32 may include a microscope objective that confocally directs and concentrates the radiation sources 22, 24 along a line to a surface 18, 20 of the support structure 16.

Biological component sites on the support structure 16 may fluoresce at particular wavelengths in response to an excitation beam and thereby return radiation for imaging. For instance, the fluorescent components may be generated by fluorescently tagged nucleic acids that hybridize to complementary molecules of the components or to fluorescently tagged nucleotides that are incorporated into an oligonucleotide using a polymerase. As noted above, the fluorescent properties of these components may be changed through the introduction of reagents into the support structure 16 (e.g., by cleaving the dye from the molecule, blocking attachment of additional molecules, adding a quenching reagent, adding an acceptor of energy transfer, and so forth). As will be appreciated by those skilled in the art, the wavelength at which the dyes of the sample are excited and the wavelength at which they fluoresce will depend upon the absorption and emission spectra of the specific dyes. Such returned radiation may propagate back through the directing optics 30. This retrobeam may generally be directed toward detection optics 34 which may filter the beam such as to separate different wavelengths within the retrobeam, and direct the retrobeam toward at least one detector 36.

The detector 36 may be based upon any suitable technology, and may be, for example, a charged coupled device (CCD) sensor that generates pixilated image data based upon photons impacting locations in the device. However, it will be understood that any of a variety of other detectors may also be used including, but not limited to, a detector array configured for time delay integration (TDI) operation, a complementary metal oxide semiconductor (CMOS) detector, an avalanche photodiode (APD) detector, a Geiger-mode photon counter, or any other suitable detector. TDI mode detection can be coupled with line scanning as described in U.S. Pat. No. 7,329,860.

The detector 36 may generate image data, for example, at a resolution between 0.1 and 50 microns, which is then forwarded to a control/processing system 38. In general, the control/processing system 38 may perform various operations, such as analog-to-digital conversion, scaling, filtering, and association of the data in multiple frames to appropriately and accurately image multiple sites at specific locations on a sample. The control/processing system 38 may store the image data and may ultimately forward the image data to a post-processing system (not shown) where the data are analyzed. Depending upon the types of sample, the reagents used, and the processing performed, a number of different uses may be made of the image data. For example, nucleotide sequence data can be derived from the image data, or the data may be employed to determine the presence of a particular gene, characterize one or more molecules at the component sites, and so forth. The operation of the various components illustrated in FIG. 1 may also be coordinated with the control/processing system 38. In a practical application, the control/processing system 38 may include hardware, firmware, and software designed to control operation of the radiation sources 22, 24, movement and focusing of the focusing optics 32, a translation system 40, and the detection optics 34, and acquisition and processing of signals from the detector 36. The control/processing system 38 may thus store processed data and further process the data for generating a reconstructed image of irradiated sites that fluoresce within the support structure 16. The image data may be analyzed by the system itself, or may be stored for analysis by other systems and at different times subsequent to imaging.

The support structure 16 may be supported on a translation system 40 which allows for focusing and movement of the support structure 16 before and during imaging. The stage may be configured to move the support structure 16, thereby changing the relative positions of the radiation sources 22, 24 and detector 36 with respect to the surface bound biological components for progressive scanning. Movement of the translation system 40 can be in one or more dimensions including, for example, one or both of the dimensions that are orthogonal to the direction of propagation for the excitation radiation line, typically denoted as the X and Y dimensions. In particular embodiments, the translation system 40 may be configured to move in a direction perpendicular to the scan axis for a detector array. A translation system 40 useful in the present invention may be further configured for movement in the dimension along which the excitation radiation line propagates, typically denoted as the Z dimension. Movement in the Z dimension can also be useful for focusing.

Figure 2:
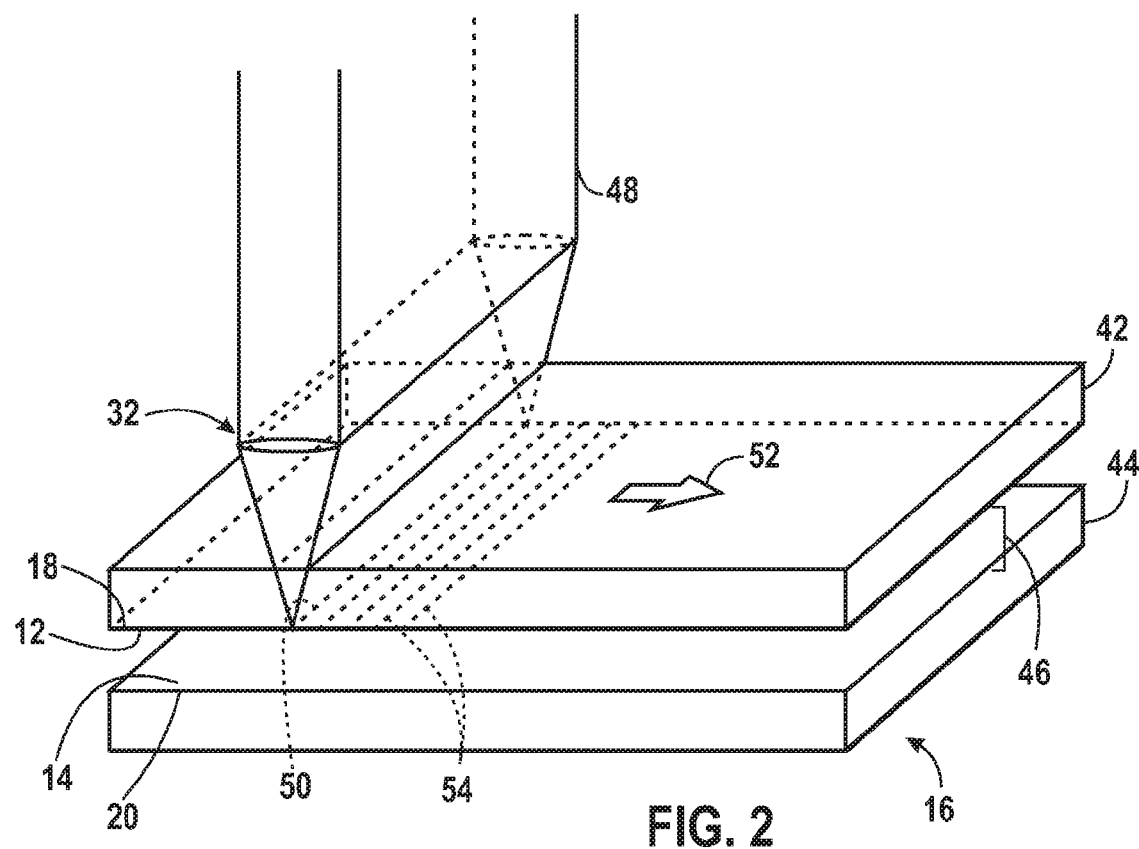
FIG. 2 is a diagrammatical perspective view of an exemplary radiation line directed toward a surface of a support structure to semi-confocally irradiate biological sites, and to semi-confocally return radiation to a detector in accordance with the present invention.

FIG. 2 is a diagrammatical representation of an exemplary semi-confocal line scanning approach to imaging the support structure 16. In the illustrated embodiment, the support structure 16 includes an upper plate 42 and a lower plate 44 with an internal volume 46 between the upper and lower plates 42, 44. The upper and lower plates 42, 44 may be made of any of a variety of materials but may preferably be made of a substrate material that is substantially transparent at the wavelengths of the excitation radiation and the fluoresced retrobeam, allowing for the passage of excitation radiation and returned fluorescent emissions without significant loss of signal quality. Moreover, when used in epifluorescent imaging arrangements as shown, one of the surfaces through which the radiation traverses may be substantially transparent at the relevant wavelengths, while the other (which is not traversed by radiation) may be less transparent, translucent, or even opaque or reflective. The upper and lower plates 42, 44 may both contain biological components 12, 14 on their respective, inwardly facing surfaces 18, 20. As discussed above, the internal volume 46 may, for instance, include one or more internal passages of a flow cell though which reagent fluids may flow.

The support structure 16 may be irradiated by excitation radiation 48 along a radiation line 50. The radiation line 50 may be formed by the excitation radiation 48 from the radiation sources 22, 24, directed by the directing optics 30 through the focusing optics 32. The radiation sources 22, 24 may generate beams that are processed and shaped to provide a linear cross section or radiation line including a plurality of wavelengths of radiation used to cause fluorescence at correspondingly different wavelengths from the biological components 12, 14, depending upon the particular dyes used. The focusing optics 32 may then semi-confocally direct the excitation radiation 48 toward the first surface 18 of the support structure 16 to irradiate sites of biological component 12 along the radiation line 50. In addition, the support structure 16, the directing optics 30, the focusing optics 32, or some combination thereof, may be slowly translated such that the resulting radiation line 50 progressively irradiates the component as indicated by the arrow 52. This translation results in successive scanning of regions 54 which allow for the gradual irradiation of the entire first surface 18 of the support structure 16. As will be discussed in more detail below, the same process may also be used to gradually irradiate the second surface 20 of the support structure 16. Indeed, the process may be used for multiple surfaces within the support structure 16.

Exemplary methods and apparatus for line scanning are described in U.S. Pat. No. 7,329,860, which is incorporated herein by reference, and which describes a line scanning apparatus having a detector array configured to achieve confocality in the scanning axis by restricting the scan-axis dimension of the detector array. More specifically, the scanning device can be configured such that the detector array has rectangular dimensions such that the shorter dimension of the detector is in the scan-axis dimension and imaging optics are placed to direct a rectangular image of a sample region to the detector array such that the shorter dimension of the image is also in the scan-axis dimension. In this way, semi-confocality can be achieved since confocality occurs in a single axis (i.e. the scan axis). Thus, detection is specific for features on the surface of a substrate, thereby rejecting signals that may arise from the solution around the feature. The apparatus and methods described in U.S. Pat. No. 7,329,860 can be modified such that two or more surfaces of a support are scanned in accordance with the description herein.

Detection apparatus and methods other than line scanning can also be used. For example, point scanning can be used as described below or in U.S. Pat. No. 5,646,411, which is incorporated herein by reference. Wide angle area detection can be used with or without scanning motion. As set forth in further detail elsewhere herein, TIR methods can also be used.

As illustrated generally in FIG. 2, the radiation line 50 used to image the sites of biological components 12, 14, in accordance with the present invention, may be a continuous or discontinuous line. As such, some embodiments of the present invention may include a discontinuous line made up of a plurality of confocally or semi-confocally directed beams of radiation which nevertheless irradiate a plurality of points along the radiation line 50. These discontinuous beams may be created by one or more sources that are positioned or scanned to provide the excitation radiation 48. These beams, as before, may be confocally or semi-confocally directed toward the first or second surfaces 18, 20 of the support structure 16 to irradiate sites of biological component 12, 14. As with the continuous semi-confocal line scanning described above, the support structure 16, the directing optics 30, the focusing optics 32, or some combination thereof, may be advanced slowly as indicated by arrow 52 to irradiate successive scanned regions 54 along the first or second surfaces 18, 20 of the support structure 16, and thereby successive regions of the sites of biological components 12, 14.

It should be noted that the system will typically form and direct excitation and returned radiation simultaneously for imaging. In some embodiments, confocal point scanning may be used such that the optical system directs an excitation point or spot across a biological component by scanning the excitation beam through an objective lens. The detection system images the emission from the excited point on the detector without "descanning" the retrobeam. This occurs since the retrobeam is collected by the objective lens and is split off the excitation beam optical path before returning back through the scan means. Therefore, the retrobeam will appear on the detector 36 at different points depending on the field angle of the original excitation spot in the objective lens. The image of the excitation point, at the detector 36, will appear in the shape of a line as the excitation point is scanned across the sample. This architecture is useful, for example, if the scan means cannot for some reason accept the retrobeam from the sample. Examples are holographic and acoustic optic scan means that are able to scan a beam at very high speeds but utilize diffraction to create the scan. Therefore, the scan properties are a function of wavelength. The retrobeam of emitted radiation is at a different wavelength from the excitation beam. Alternatively or additionally, emission signals may be collected sequentially following sequential excitation at different wavelengths.

In particular embodiments, an apparatus or method of the invention can detect features on a surface at a rate of at least about 0.01 mm$^2$/sec. Depending upon the particular application of the invention, faster rates can also be used including, for example, in terms of the area scanned or otherwise detected, a rate of at least about 0.02 mm$^2$/sec, 0.05 mm$^2$/sec, 0.1 mm$^2$/sec, 1 mm$^2$/sec, 1.5 mm$^2$/sec, 5 mm$^2$/sec, 10 mm$^2$/sec, 50 mm$^2$/sec, 100 mm$^2$/sec, or faster. If desired, for example, to reduce noise, the detection rate can have an upper limit of about 0.05 mm$^2$/sec, 0.1 mm$^2$/sec, 1 mm$^2$/sec, 1.5 mm$^2$/sec, 5 mm$^2$/sec, 10 mm$^2$/sec, 50 mm$^2$/sec, or 100 mm$^2$/sec.

Figure 3:
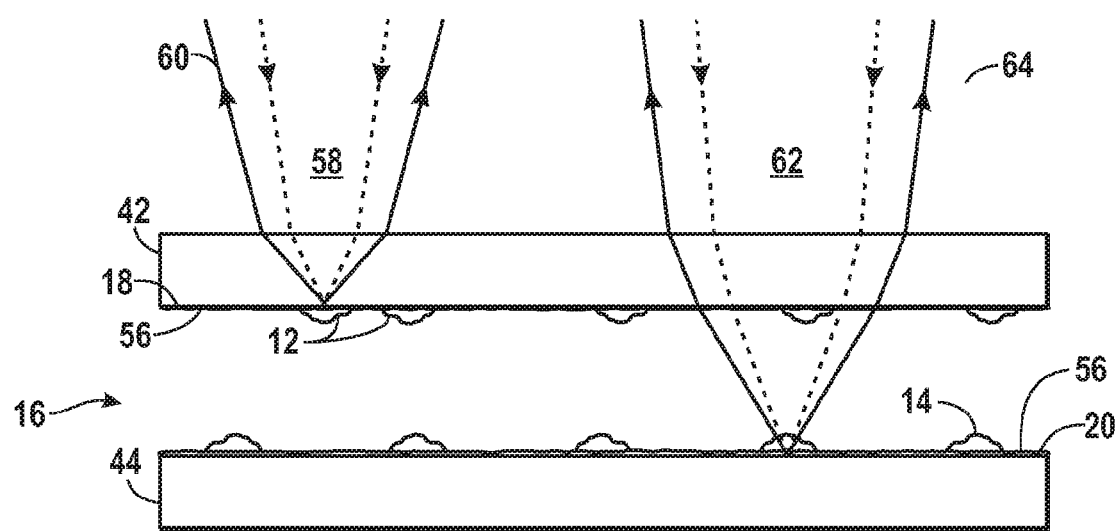
FIG. 3 is a sectional view of an exemplary support structure with excitation radiation directed at two surfaces of the support structure in accordance with the present invention.

In some instances, the support structure 16 may be used in such a way that biological components are expected to be present on only one surface. However, in many instances, biological material is present on multiple surfaces within the support structure 16. For instance, FIG. 3 illustrates a typical support structure 16 where biological material has attached to the first surface 18 as well as to the second surface 20. In the illustrated embodiment, an attachment layer 56 has formed on both the first surface 18 and the second surface 20 of the support structure 16. A first excitation radiation 58 source may be used to irradiate one of many sites of biological component 12 on the first surface 18 of the support structure 16 and return a first fluorescent emission 60 from the irradiated biological component 12. Simultaneously or sequentially, a second source of excitation radiation 62 may be used to irradiate one of many sites of biological component 14 on the second surface 20 of the support structure 16, and return a second fluorescent emission 64 from the irradiated biological component 14.

Although the embodiment exemplified in FIG. 3 shows excitation from source 58 and source 62 coming from the same side of the support structure 16, it will be understood that the optical system can be configured to impinge on the surfaces from opposite sides of the support structure 16. Taking FIG. 3 as an example, upper surface 18 can be irradiated from excitation source 58 as shown and the lower surface 20 can be irradiated from below. Similarly, emission can be detected from one or more sides of a support structure. In particular embodiments, different sides of the support structure 16 can be excited from the same radiation source by first irradiating one side and then flipping the support structure to bring another side into position for excitation by the radiation source.

Figure 4:
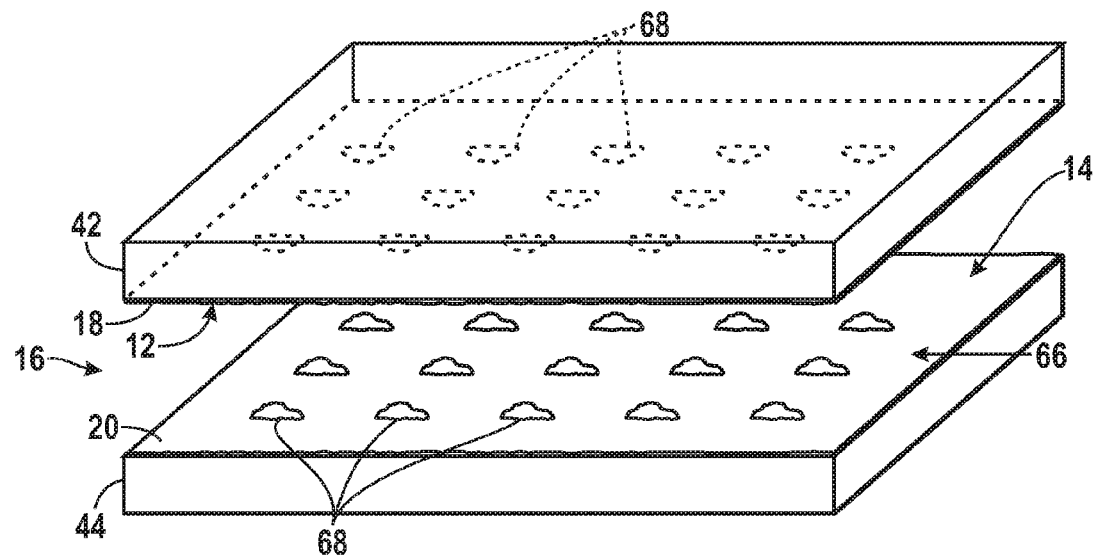
FIG. 4 is a diagrammatical perspective view of an exemplary support structure having an array of biological component sites in a spatially ordered pattern in accordance with the present invention.

The distribution of biological components 12, 14 may follow many different patterns. For instance, FIG. 4 illustrates a support structure 16 where the biological components 12, 14 at sites or features on the first and second surfaces 18, 20 are distributed evenly in a spatially ordered pattern 66 of biological component sites 68. For example, certain types of microarrays may be used where the location of individual biological component sites 68 may be in a regular spatial pattern. The pattern can include sites at pre-defined locations. In contrast, in other types of biological imaging arrays, biological components attach to surfaces at sites that occur in random or statistically varying positions such that imaging the microarray is used to determine the location of each of the individual biological component features. Thus, the pattern of features need not be pre-determined despite being the product of a synthetic or manufacturing process.

Figure 5:
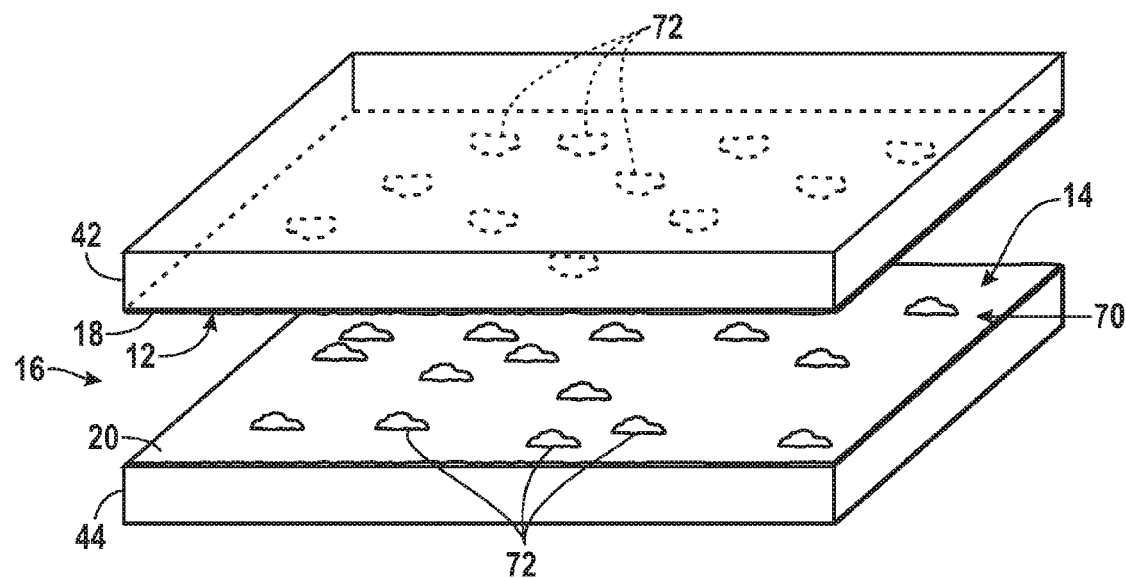
FIG. 5 is a diagrammatical perspective view of an exemplary support structure having biological component sites in a random spatial distribution in accordance with the present invention.

For instance, FIG. 5 illustrates a support structure 16 where the sites on the first and second surfaces 18, 20 are located in a random spatial distribution 70 of biological component sites 72. However, with both fixed arrays 66 and random distribution 70 of biological sample sites, imaging of multiple surfaces 18, 20 of the support structure 16 may be possible. In addition, it should be noted that in both instances, the biological components at the individual sites may constitute either a population of identical molecules or a random mix of different molecules. Furthermore, the density of biological samples may vary and may be at least 1,000 sites per square millimeter.

The present techniques accommodate such varied physical arrangements of the multiple surfaces within the support structure 16, as well as the varied disposition of the sites within components on the surfaces. As discussed above with reference to FIGS. 2 and 3, in the embodiments with a support structure 16 having a first surface 18 and a second surface 20, a first source of excitation radiation 58 may irradiate sites of biological component 12 on the first surface 18, and return a first fluorescent emission 60, while a second source of excitation radiation 62 may irradiate sites of biological component 14 on the second surface 20 and return a second fluorescent emission 64 source, as illustrated in FIG. 3. Thus, components of the volume of sample between two surfaces need not be detected and can be rejected. Selective detection of a surface of a support structure provides preferential detection of the surface compared to the volume of the support structure adjacent the surface and compared to one or more other surfaces of the support structure.

Figure 6:
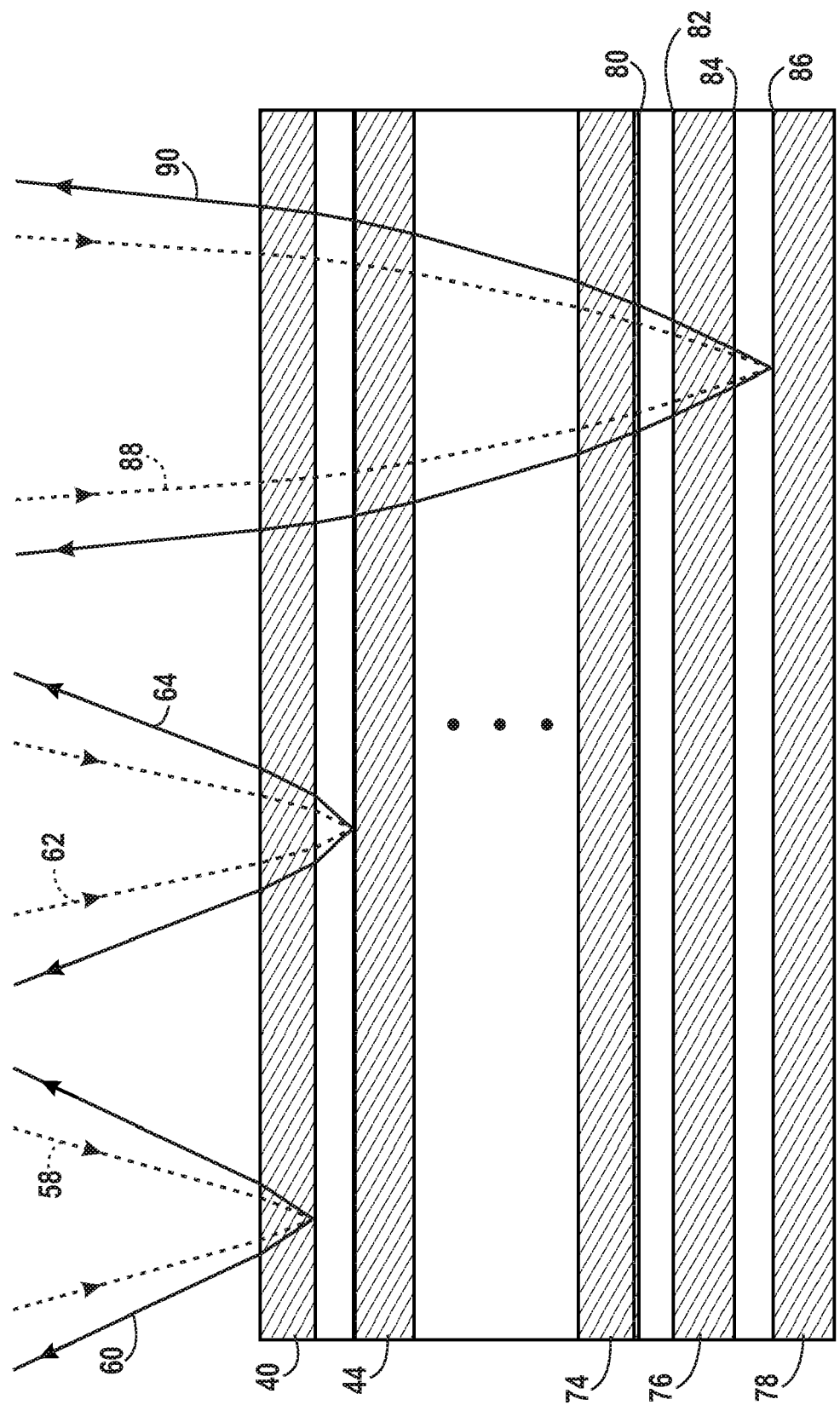
FIG. 6 is a sectional view of an exemplary support structure with excitation radiation directed at multiple surfaces of the support structure in accordance with the present invention.

In more complex configurations, it may be useful to irradiate more than two surfaces. For instance, FIG. 6 illustrates a support structure 16 having N number of plates including a first plate 42, a second plate 44, ..., an N-2 plate 74, an N-1 plate 76, and an N plate 78. These plates define M number of surfaces including a first surface 18, a second surface 20, ..., an M-3 surface 80, an M-2 surface 82, an M-1 surface 84, and an M surface 86. In the illustrated embodiment, not only the first surface 18 and the second surface 20 of the support structure 16 may be irradiated but, rather, all M number of surfaces may be irradiated. For instance, a source of excitation radiation 88 may be used to irradiate biological component sites on the $M^{th}$ surface 86 of the support structure 16 and return a fluorescent emission 90 from the irradiated biological component. For support structures having a plurality of surfaces it may be desirable to excite upper layers from the top and lower layers from the bottom to reduce photobleaching. Thus, components on layers that are closer to a first exterior side of a support structure can be irradiated from the first side, whereas irradiation from the opposite exterior side can be used to excite components present on layers that are closer to the opposite exterior side.

Figure 7:
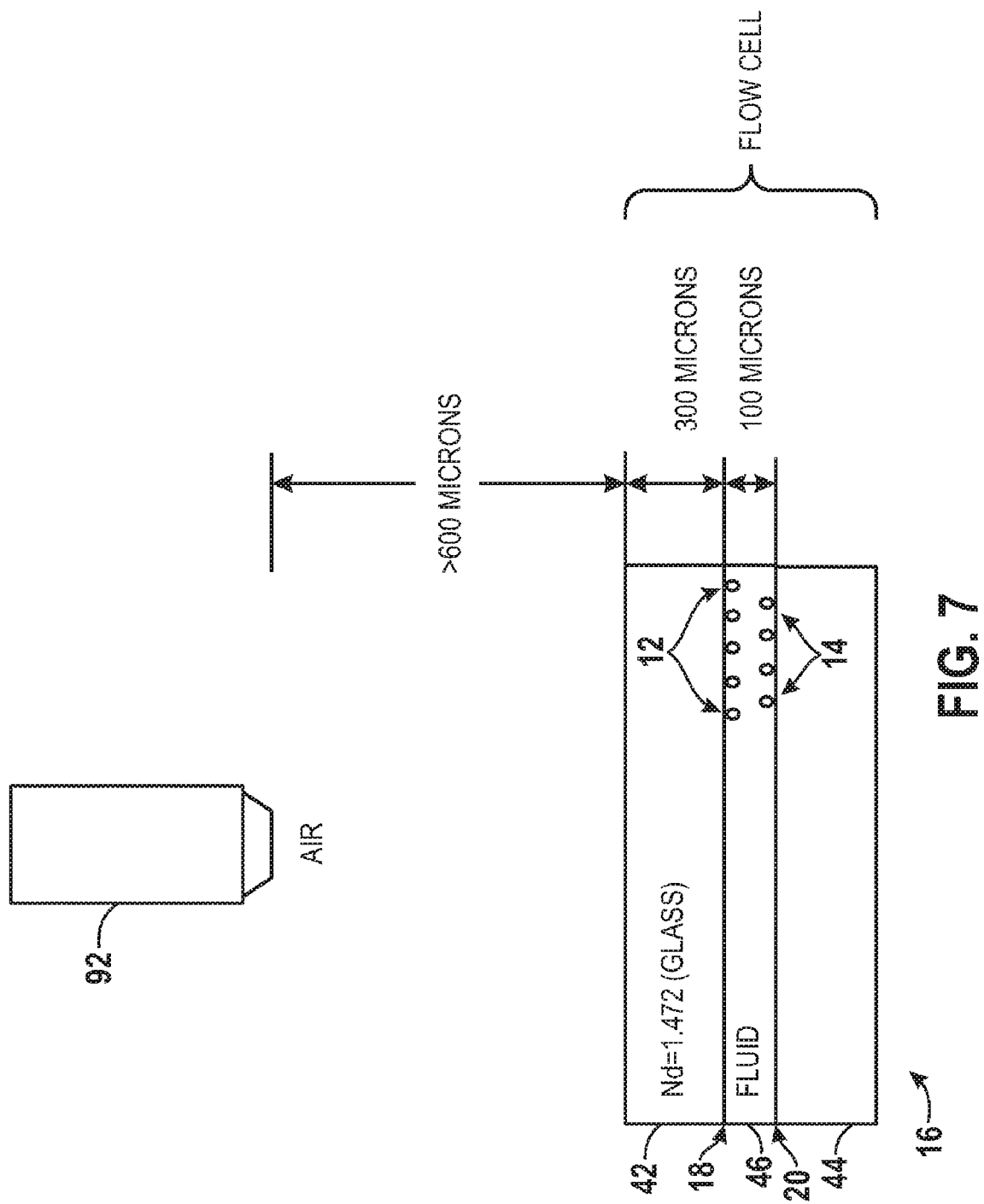
FIG. 7 illustrates exemplary dimensions between the objective and the support structure in accordance with the present invention.

FIG. 7 illustrates an objective 92 through which radiation from emissive biological components 12, 14 on first and second surfaces 18, 20, respectively, of the support structure 16 may be detected. The objective 92 may be one of the components of the focusing optics 32 described above. Although not drawn to scale, FIG. 7 illustrates exemplary dimensions between the objective 92 and the support structure 16. For instance, the objective 92 may typically be spaced approximately 600 or more microns from the upper plate 42 of the support structure 16. The biological sample imaging system 10 may be configured to detect emitted radiation from biological components 12 on the first surface 18 through 300 microns of the upper plate 42 which may, for instance, be made of glass and may have a refractive index $N_d$ of 1.472. In addition, the biological sample imaging system 10 may also be configured to detect emitted radiation from biological components 14 on the second surface 20 through 300 microns of the upper plate 42 plus 100 microns of the fluid within the internal volume 46 of the support structure 46.

In certain embodiments, the objective 92 may be designed for diffraction-limited focusing and imaging on only one of the first or second surfaces 18, 20 of the support structure 16. For example throughout the present description of FIGS. 7 through 14, the objective 92 may be designed for pre-compensation of the 300 microns of the upper plate 42 plus the 100 micron read buffer of the fluid within the internal volume 46 of the support structure 16. In such a scenario, diffraction-limited performance may only be possible on the second surface 20. Furthermore, the spherical aberration introduced by the 100 micron read buffer may severely impact the imaging quality when imaging from the first surface 18. However, reducing the lane thickness of the internal volume 46 of the support structure 16 might increase the amount of surface-to-surface "crosstalk." Therefore, perhaps the most appropriate solution is to correct the aberration. As such, it may be necessary to use a compensator capable of achieving diffraction-limited imaging performance on both the first and second surfaces 18, 20 of the support structure 16.

It should be noted that the need for a compensator may be more pronounced when using objectives 92 with high numerical aperture (NA) values. Exemplary high NA ranges for which the invention is particularly useful include NA values of at least about 0.6. For example, the NA may be at least about 0.65, 0.7, 0.75, 0.8, 0.85, 0.9, 0.95, or higher. Those skilled in the art will appreciate that NA, being dependent upon the index of refraction of the medium in which the lens is working, may be higher including, for example, up to 1.0 for air, 1.33 for pure water, or higher for other media such as oils. The compensator may also find use in objectives having lower NA values than the examples listed above. In general, the NA value of an objective 92 is a measure of the breadth of angles for which the objective 92 may receive light. The higher the NA value, the more light that may be collected by the objective 92 for a given fixed magnification. This is because the collection efficiency and the resolution increase. As a result, multiple objects may be distinguished more readily when using objectives 92 with higher NA values because a higher feature density may be possible. Therefore, in general, a higher NA value for the objective 92 may be beneficial for imaging. However, as the NA value increases, its sensitivity to focusing and imaging-through media thickness variation also increases. In other words, lower NA objectives 92 have longer depth of field and are generally not as sensitive to changes in imaging-through media thickness.

Figure 8:
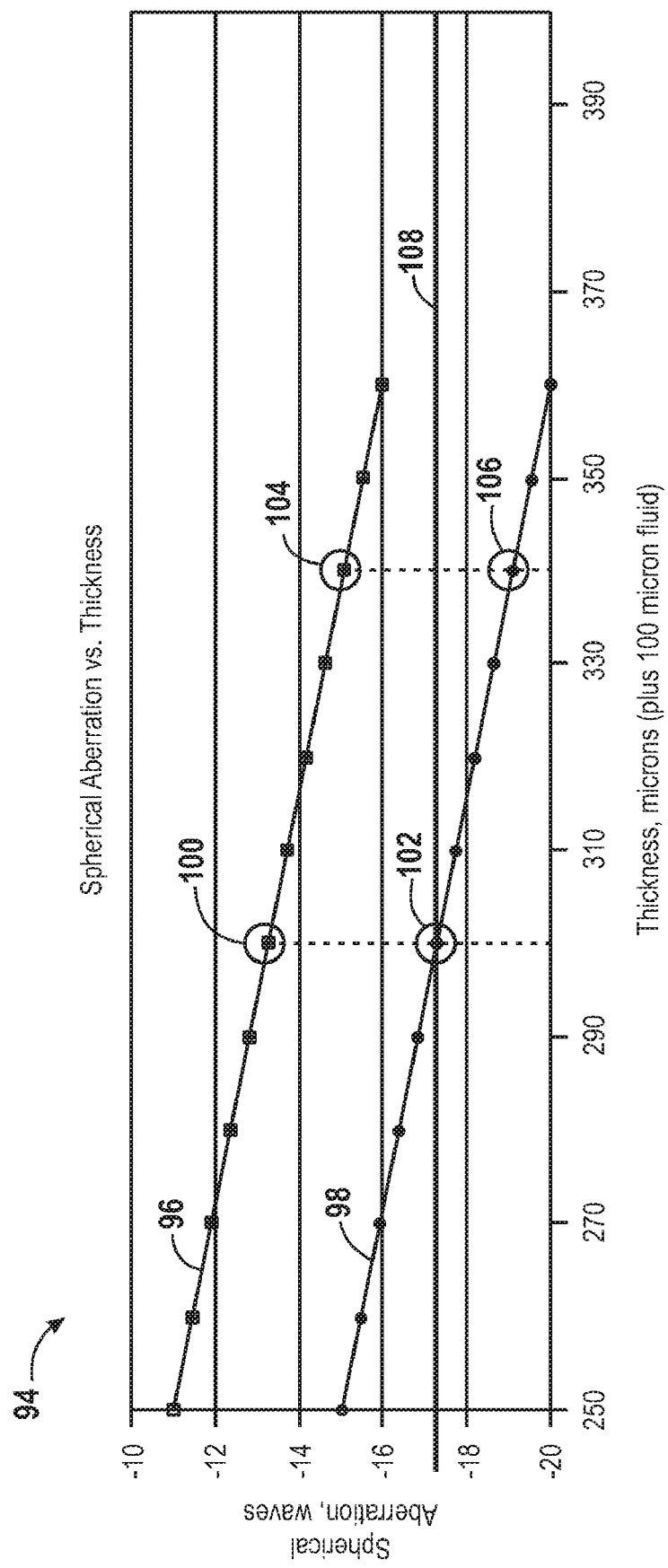
FIG. 8 is an exemplary chart of spherical aberration vs. thickness of the upper plate of the support structure of FIG. 7 in accordance with the present invention.
Figure 9B:
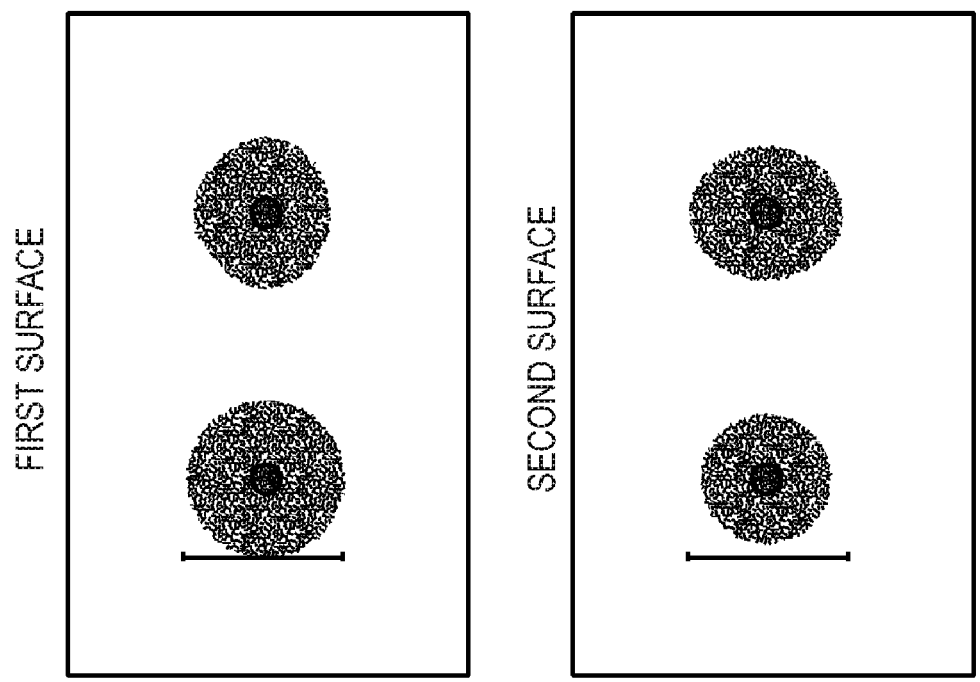
FIG. 9B illustrates exemplary images expected for first and second surfaces of a support structure when obtained through an upper surface thickness of 340 microns (plus 100 microns of fluid) without corrective optics.
Figure 9A:
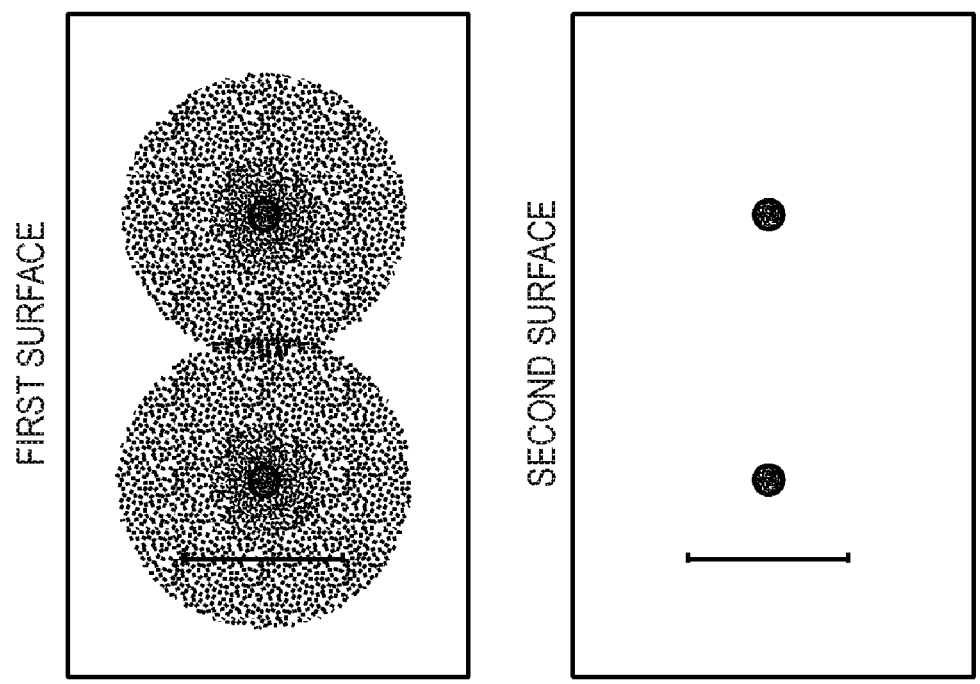
FIG. 9A illustrates exemplary images expected for first and second surfaces of a support structure when obtained through an upper surface thickness of 300 microns (plus 100 microns of fluid) without corrective optics, where the imaging system is optimized for the second surface.

FIG. 8 is an exemplary chart 94 of spherical aberration (in waves) vs. thickness (in microns) of the upper plate 42 of the support structure 16 of FIG. 7 in accordance with the present invention. Specifically, the upper line 96 of the graph depicts the amount of spherical aberration of an image taken from biological components 12 on the first surface 18 of the support structure 16 while the lower line 98 of the graph depicts the amount of spherical aberration of an image taken from biological components 14 on the second surface 20 of the support structure 16. In the illustrated embodiment, the spherical aberration generated by the 100 micron read buffer is around 4 waves, which is much higher than the diffraction-limited performance requirement of less than 0.25 waves, for instance. As illustrated, at 300 microns (i.e. the thickness of the upper plate 42), the spherical aberration for the first surface 18 is around −13.2 waves (e.g., point 100) while the spherical aberration for the second surface 20 is around −17.2 waves (e.g., point 102). FIG. 9A illustrates exemplary images expected for the first and second surfaces 18, 20 of the support structure 16 corresponding to the thickness of the upper plate 42 (i.e., 300 microns) in accordance with the present invention, where the imaging system is optimized for the second surface 20 (pre-compensated for −17.2 waves). As shown, the imaging system is capable of providing high image quality on the second surface 20 since, according to the present scenario, it was designed to do so. However, the images taken for the first surface 18 contain aberrations.

To balance out the spherical aberration, it is beneficial to introduce an additional thickness (e.g., by introducing an additional coverslip) between the objective 92 and the support structure 16. For instance, returning now to FIG. 8, if an additional thickness of approximately 40 microns were to be introduced between the objective 92 and the first and second surfaces 18, 20 of support structure 16, the difference between the spherical aberrations at the design thickness (i.e., 300 micron upper plate plus 100 microns of fluid) may be split such that the image produced for both the first and second surfaces 18, 20 may have similar quality. For instance, as illustrated, at 340 microns (i.e. the thickness of the upper plate 42 plus an additional 40 micron thickness), the spherical aberration for the first surface 18 is around −15.2 waves (e.g., point 104) while the spherical aberration for the second surface 20 is around −19.2 waves (e.g., point 106), splitting the difference of −17.2 waves (e.g., point 108) which may be characterized as the design point for the objective 92. FIG. 9B illustrates exemplary images expected for the first and second surfaces 18, 20 of the support structure 16 corresponding to the thickness of the upper plate 42 plus an additional thickness (i.e., 300 microns plus 40 microns) in accordance with the present invention, illustrating how the additional thickness may allow for balance between images taken for the first and second surfaces 18, 20 of the support structure 16.

However, merely introducing an additional thickness between the objective 92 and the support structure 16 may not be desired for all uses of the imaging system set forth herein. For instance, as illustrated in FIGS. 9A and 9B, by simply introducing the additional 40 micron thickness between the objective 92 and the support structure 16, images from both the first and second surfaces 18, 20 may still experience residual aberration from the design point 108 of the objective 92. Therefore, a more precise solution may be to only introduce the additional thickness when detecting radiation from biological components 12 on the first surface 18 of the support structure 16. In such a scenario, the spherical aberration corresponding to the design point 108 of the objective 92 may generally be achieved for both the first and second surfaces 18, 20. It should be noted that the particular dimensions and measurements (e.g., thicknesses, spherical aberration values, and so forth) described with respect to FIGS. 9A and 9B are merely intended to be exemplary of the manner in which the present invention functions. As such, these dimensions and measurements are not intended to be limiting. Indeed, the particular geometries and resulting measurement values may vary between implementations.

For example, FIG. 10A illustrates an exemplary objective 92 imaging the second surface 20 of the support structure 16 without the assistance of a compensator 110 in accordance with the present invention. Without the compensator 110, the objective 92 may focus and detect images from the second surface 20 of the support structure 16 according to its design and experiencing the design spherical aberration. However, FIG. 10B illustrates an exemplary objective 92 imaging the first surface 20 of the support structure 16 with the assistance of a compensator 110 in accordance with the present invention. By using the compensator 110 (e.g., similar to the additional 40 micron thickness described above with respect to FIGS. 8 and 9), the objective 92 may focus and detect images from the first surface 18 of the support structure 16 under similar conditions to that of its design point for the second surface 20 of the support structure 16. Therefore, by detecting images for the second surface 20 without the compensator 110 and detecting images for the first surface 18 with the compensator 110, the objective 92 may be capable of detecting images on both surfaces with diffraction-limited performance similar to the design of the objective 92.

The chromatic shift curve may be limited to wavelength ranges of between 530 nm to 780 nm. Chromatic shifts of different color wavelength bands may be compensated for by focusing the focusing optics 32 in each band. The compensator 110 should preferably be "invisible" to the focusing optics 32. In other words, the compensator 110 should correct the spherical aberration difference of the read buffer but should maintain the chromatic shift curve in the wavelength range of 530-780 nm. More specifically, the chromatic shift relationships among the peak wavelengths of 560 nm, 610 nm, 687 nm, and 720 nm should be maintained. In addition, other specifications, including NA, field curvature, field distortion, detection magnification, and so forth, should also be maintained. Furthermore, the compensator 110 package should be relatively small (e.g., no more than 10 mm of total thickness). Moreover, insensitivity to positioning error of the compensator 110 may be preferred.

Several various designs may be implemented to introduce the corrective optics of the compensator 110 into the optical train of the imaging optics of the biological sample imaging system 10. For example, FIG. 11 is an exemplary compensator 110 design, incorporating a first objective 92 and a second objective 112 which may replace the first objective 92 in the optical train in accordance with the present invention. In the illustrated embodiment, each respective objective 92, 112 may contain the optics required to image respective surfaces, such as the first and second surfaces 18, 20 of the support structure 16. For instance, the first objective 92 may contain the imaging optics necessary to focus on and image emissive biological components 14 on the second surface 20 of the support structure 16 while the second objective 112 may contain the imaging optics plus the corrective optics necessary to focus on and image emissive biological components 12 on the first surface 18 of the support structure 16. In operation, the first objective 92 may detect images from the second surface 20 of the support structure 16. The first objective 92 may be replaced by the second objective 112 in the optical train, at which point the second objective 112 may detect images from the first surface 18 of the support structure 16. An advantage of the embodiment illustrated in FIG. 11 is that the optics may be decoupled and may operate independently. However, a disadvantage in some situations is that having two entirely separate objectives 92, 112 may not be cost-effective since certain components may be duplicated for each objective 92, 112. Furthermore, in embodiments where multiple images of an object are obtained, the use of two objectives may increase the computational resources required for registration between images. In particular embodiments, imaging of both surfaces may occur through the same objective to provide particular advantages as set forth below. In other words, the first objective 92 need not be removed or replaced with the second objective 112 for imaging of the different surfaces.

FIG. 12 is another exemplary compensator 110 design, incorporating a corrective device 114 which may be inserted between the objective 92 and the support structure 16 in accordance with the present invention. The corrective device 114 may, for instance, be a coverslip or other thin layer of glass. As illustrated, the corrective device 114 may simply be inserted into and removed from the optical path between the objective 92 and the support structure 16 depending on the particular surface 16 being imaged. For instance, the corrective device 114 may be removed from the optical path when the objective 92 is used to focus on and image emissive biological components 14 on the second surface 20 of the support structure 16. Conversely, the corrective device 114 may be inserted into the optical path when the objective 92 is used to focus on and image emissive biological components 12 on the first surface 18 of the support structure 16. An advantage of the embodiment illustrated in FIG. 12 is that it is relatively straightforward. The required additional compensator thickness may simply be inserted into the optical path. Typically, the corrective device 114 may be placed such that it does not physically contact the support structure 16 or the objective 92.

FIG. 13 is another exemplary compensator 110 design, incorporating a correction collar 116 in accordance with the present invention. In the illustrated embodiment, the correction collar 116 may be adjusted between binary states. For instance, the first state 118 may correspond to the situation where the objective 92 is focused on and detecting images from the second surface 20 of the support structure 16 while the second state 120 may correspond to the situation where the objective 92 is focused on and detecting images from the first surface of the support structure 16. As such, when the correction collar 116 is in the first state 118, the imaging optics within the objective 92 may not include the corrective optics within the optical path. Conversely, when the correction collar 116 is in the second state 120, the imaging optics within the objective 92 may include the corrective optics within the optical path. Although illustrated as consisting of binary states 118, 120, the correction collar 116 may, in fact, include multiple states. For instance, when more than two surfaces of the support structure 16 are used for imaging, the correction collar 116 may be configured to adjust between multiple states such that the imaging and corrective optics vary for each respective surface of the support structure 16. An advantage of the embodiment illustrated in FIG. 13 is that it may be relatively easy to operate. For instance, the correction collar 116 may simply be adjusted between states whenever different surfaces of the support structure 16 are being imaged.

FIG. 14 is another exemplary compensator 110 design, incorporating an infinite space compensator 122 in accordance with the present invention. This embodiment is somewhat similar to the corrective device 114 embodiment of FIG. 12 in that the infinite space compensator 122 may be inserted into and removed from the optical path. However, a main difference between the embodiments is that, in the embodiment of FIG. 14, there may be more space available (e.g., up to 10 mm, as opposed to 600 microns in the embodiment of FIG. 12) within which to insert the infinite space compensator 122 into the optical path. Therefore, the embodiment of FIG. 14 may allow for greater flexibility than the corrective device 114 embodiment of FIG. 12.

In addition to the embodiments presented in FIGS. 11 through 14, there may be other compensator 110 designs which may prove beneficial. For instance, a fluidic corrector may be inserted between the objective 92 and the support structure 16. In this fluidic corrector design, the fluidic corrector may be filled with a fluid, which may effectively act as the compensator 110. The optics may be configured such that the fluid matches the upper surface of the support structure 16 and, in the absence of fluid air, matches the bottom surface of support structure 16. This design may prove beneficial in that it may make automation easier since the fluid would simply be inserted into and extracted from the fluidic corrector depending on which surface is imaged.

Regardless of the particular embodiment selected, all of the embodiments disclosed herein are characterized by repeatability and the ability to automate the use of the embodiments. These are important considerations in that the embodiments allow for the detection of images from biological components 12, 14 on multiple surfaces 18, 20 of the support structure 16 in an automated fashion. This may allow not only for increased imaging production but may also allow for greater flexibility in switching between the multiple surfaces, depending on the particular imaging needs.

As described in greater detail above, a support structure 16 useful in the apparatus or methods set forth herein can have two or more surfaces upon which a biological component is attached. In particular embodiments, the surface is a fabricated surface. Any of a variety of surfaces known in the art can be used including, but not limited to, those used for making arrays as set forth above. Examples include, glass, silicon, polymeric structures, plastics, and the like. Surfaces and flow cells that are particularly useful are described in PCT Publication No. WO 2007/123744, which is incorporated herein by reference. The surfaces of a support structure can have the same or different properties. For example, in the embodiment shown in FIG. 3, plate 42 can be transparent to the excitation and emission wavelengths used in a detection method, whereas plate 44 can optionally be transparent or opaque to the excitation or emission wavelengths. Accordingly, the surfaces can be made of the same material or the two or more surfaces can be made of different materials.

Figure 15:
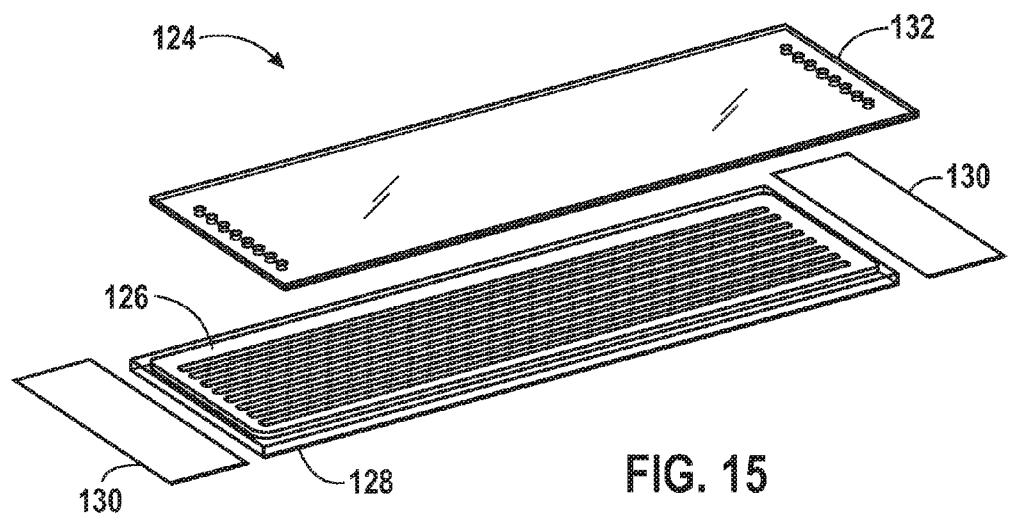
FIG. 15 is a perspective view of an exemplary flow cell assembly using patterned adhesives to form channel characteristics in accordance with the present invention.
Figure 16:
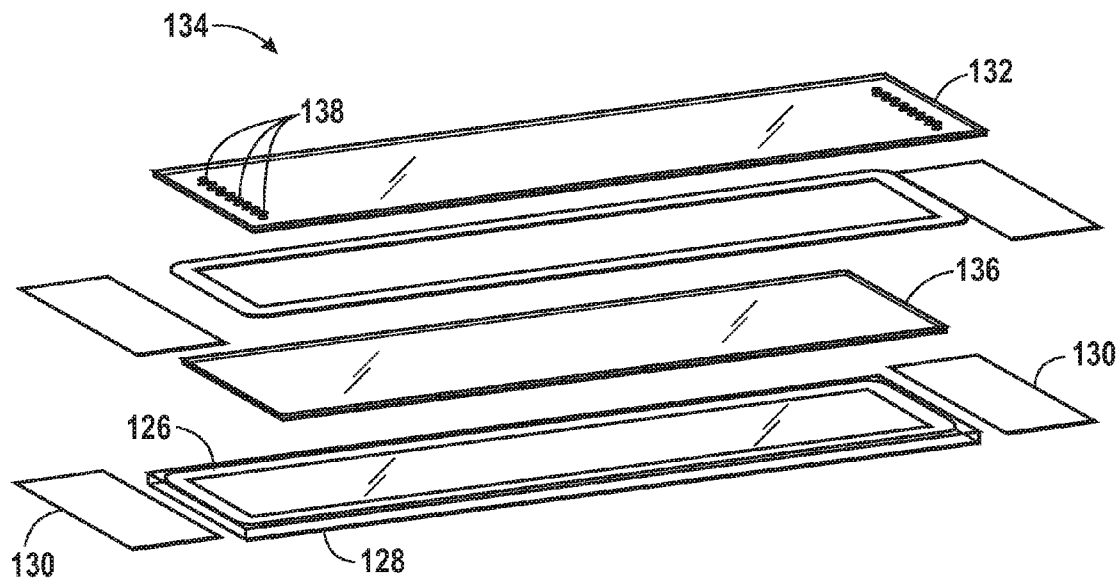
FIG. 16 is a perspective view of another exemplary flow cell assembly using patterned adhesives to form channel characteristics in accordance with the present invention.

A support structure having two or more surfaces can be formed by adhering the surfaces to each other or to other supports. For example, an adhesive material, such as epoxy resin, can be dispensed in the form of a paste onto a planar substrate in a pattern forming one or more channel characteristics of a flow cell. An exemplary flow cell 124 is shown in FIG. 15. Utilizing a programmable, automated adhesive dispenser, such as the Millennium® M-2010 from Asymtek Corp., Carlsbad Calif., a desired pattern of adhesive 126 can be designed and laid down onto the surface of a planar lower substrate 128. The thickness of the flow cell (and cross sectional height in the fluidic channels) can be set by means of precision mechanical spacers 130 placed between the lower substrate 128 and an upper substrate 132. Another exemplary flow cell 134 is shown in FIG. 16. To create a multi-layer cell, an interim transparent substrate layer 136, shorter in length than the lower and upper substrate layers 128, 132 can be included. The shorter length allows fluidic access to both/all layers from ports 138 passing through only one substrate. This intermediate layer 136 bifurcates the flow cell cavity horizontally and nearly doubles the available surface area for the attachment of biologically interesting molecules.

Figure 17:
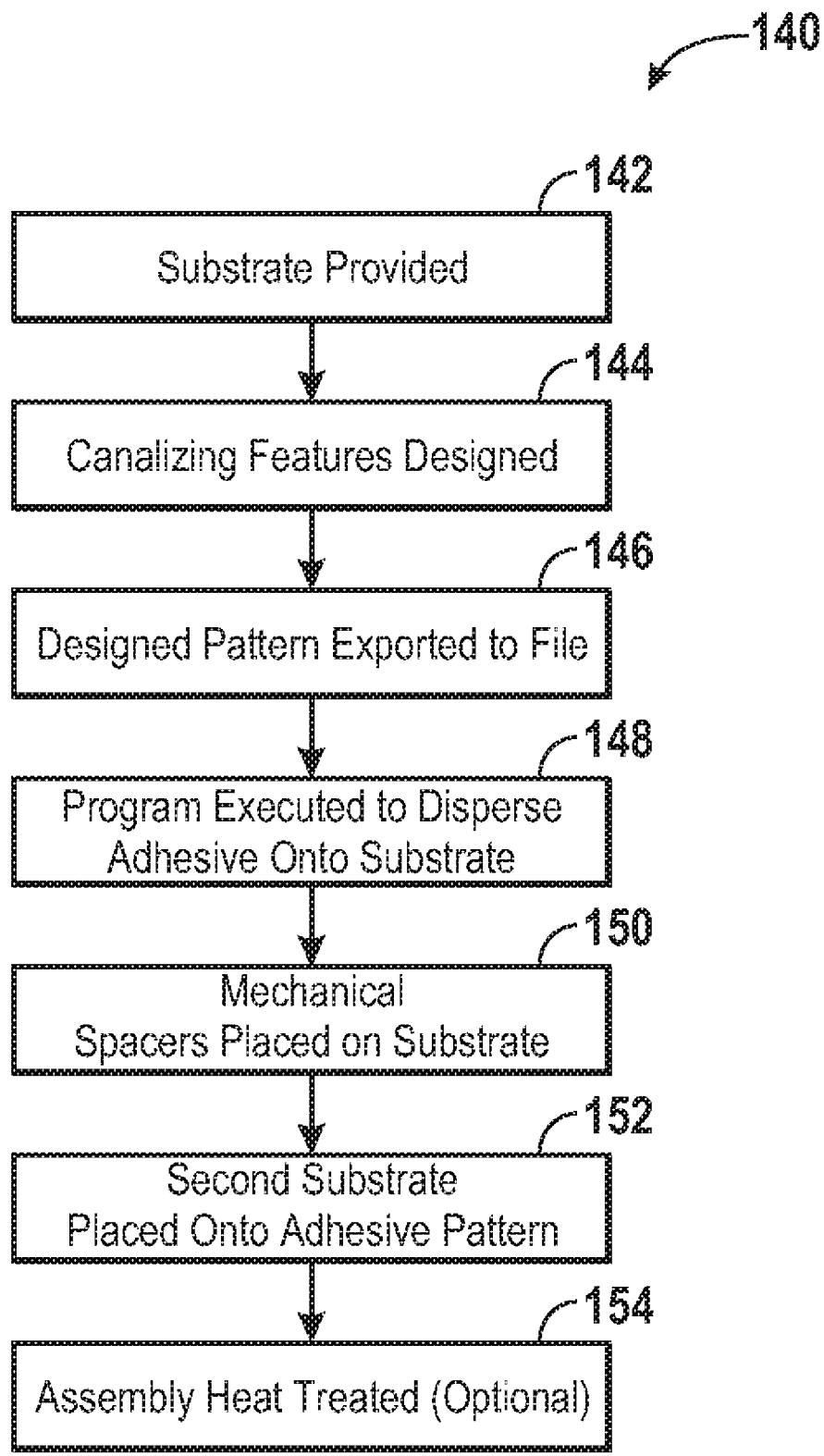
FIG. 17 is a process flow diagram of an exemplary method of assembling flow cells using patterned adhesives to form channel characteristics in accordance with the present invention.

An exemplary method 140 for fabricating such a flow cell is shown in FIG. 17. A planar substrate acting as the structural base of the cell is provided (block 142). Desired canalizing features of the cell are designed, for example, using a computer assisted design program (block 144). A pattern designed in this way can be exported to a file compatible with driving an automatic adhesive dispensing system (block 146). A program can be executed to dispense the adhesive in the desired pattern onto the substrate (block 148). Precision mechanical spacers can be placed onto the base substrate before or after the adhesive is dispensed (block 150). A second transparent substrate can then be placed onto the adhesive pattern, pressing downward until the lower surface is in full contact with the mechanical spacers (block 152). A weight or other force is applied to the top substrate to hold it in full contact with the adhesive. The spacers will typically have a height that is equivalent or slightly less than the height of the adhesive layer such that bonding can occur without causing undesirable aberrations in the shape of the canalized features. The steps for adhering substrates may be repeated for any number of layers desired. Optionally, the assembly can be heat treated, for example, in an oven or exposed to UV light, depending upon the cure requirements of the adhesive (block 154).

Another exemplary method for fabricating a flow cell is to use an intermediate layer that is cut to a desired pattern in place of an adhesive layer. A particularly useful material for the intermediate layer is silicone. The silicone layer can be heat bonded to the lower substrate 128 and upper substrate 132. Exemplary methods utilizing Bisco Silicone HT 6135 as an intermediate layer are described, for example, in Grover et al., Sensors and Actuators B 89:315-323 (2003).

Still further, FIG. 18 illustrates an embodiment utilizing one radiation source and dual detectors. Radiation from the radiation source 22 is directed by the directing optics 30 toward the focusing optics 32. From the focusing optics 32, the excitation radiation 58 irradiates a biological component 12 on a first surface 18 of the support structure 16. The biological component 12 emits a fluorescent emission 60 back through the focusing optics 32 toward the directing optics 30. This retrobeam is allowed to pass through the directing optics 30 to the detection optics 34 which, in this illustrated embodiment, may include a wavelength filter 156 or some other device for separating the retrobeam, and first and second color filters 158, 160 for achieving multiple color channels. The wavelength filter 156 may split the retrobeam into two beams with one beam directed toward the first detector 36 via the first color filter 158 and the other beam directed toward a second detector 162 via the second color filter 160. In this manner, the biological sample imaging system 10 may sequentially scan the first and second surfaces 18, 20, first scanning the first surface 18 of the support structure 16 using the first excitation radiation 58 from the radiation source 22 and the returned first fluorescent emission 60 (as depicted in the left portion of FIG. 18), and next scanning the second surface 20 of the support structure 16 using the second excitation radiation 62 from the same radiation source 22 and the returned second fluorescent emission 64 (as depicted in the right portion of FIG. 18).

Alternatively, FIG. 19 illustrates an embodiment utilizing dual radiation sources and dual detectors. Again, the two surfaces 18, 20 of the support structure 16 may be scanned sequentially. However, in this embodiment, the first surface 18 of the support structure 16 is first scanned using the first radiation source 22 which generates the first excitation radiation 58 and the first fluorescent emission 60 (as depicted in the left portion of FIG. 19) and, the second surface 20 of the support structure 16 is scanned using the second radiation source 24 which generates the second excitation radiation 62 and the second fluorescent emission 64 (as depicted in the right portion of FIG. 19). This embodiment may also be extended to use any number of detectors in order to reduce movement of the filters.

In the embodiments described above where scanning of the first and second surfaces 18, 20 of the support structure 16 may be performed sequentially, the individual steps of scanning the first and second surfaces 18, 20 of the support structure 16 may be performed in a number of ways. For instance, it may be possible to scan a single line of the first surface 18, then scan a single line of the second surface 20, then gradually move the first and second surfaces 18, 20 relative to the excitation radiation 58, 62 by translating the support structure 16, the directing optics 30, the focusing optics 32, or some combination thereof, in order to repeat these steps of scanning individual lines. Alternatively, entire regions of the first surface 18 may be scanned before regions of the second surface 20 are scanned. The individual processing steps taken may depend upon several variables including the particular configuration of the biological component sites 12, 14 on the surfaces 18, 20 as well as other variables, including environmental and operating conditions.

Figure 20:
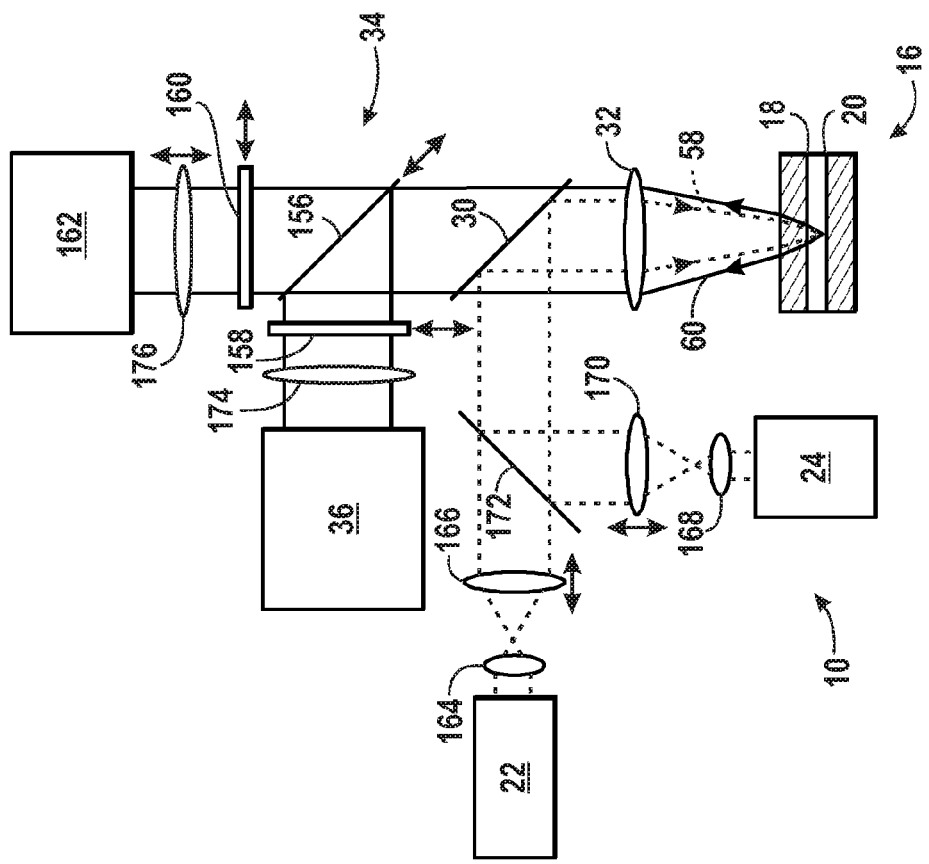
FIG. 20 is a diagrammatical view of a biological sample imaging system with dual radiation sources and dual detectors configured to simultaneously scan multiple surfaces of the support structure using focusing lenses along the excitation path in accordance with the present invention.

Particular embodiments may allow for simultaneous excitation of multiple surfaces of the support structure 16. For instance, FIG. 20 illustrates an embodiment utilizing dual radiation sources and dual detectors. However, in this embodiment, the first surface 18 and the second surface 20 of the support structure 16 may be simultaneously scanned. This may be accomplished using focusing lenses 164, 166, 168, 170 and a dichroic mirror 172 along the excitation path in order to switch surfaces and filters 158, 160 to achieve multiple color channels. Again, this illustrated embodiment may also be extended to any number of detectors to improve throughput, scanning efficiency, and to reduce movement of the filters and other system components.

Figure 21:
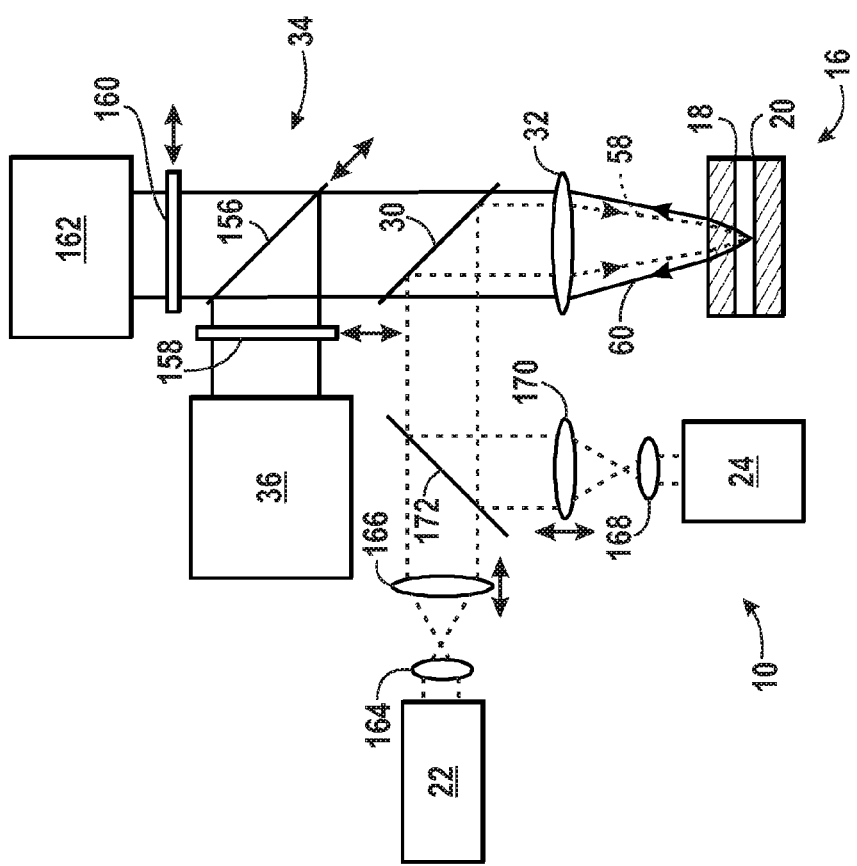
FIG. 21 is a diagrammatical view of a biological sample imaging system with dual radiation sources and dual detectors configured to simultaneously scan multiple surfaces of the support structure using focusing lenses along the excitation and emission paths in accordance with the present invention.

FIG. 21 illustrates another embodiment utilizing dual radiation sources and dual detectors which allows for simultaneous scanning of the first and second surfaces 18, 20 of the support structure 16. In this illustrated embodiment, however, not only are focusing lenses 164, 166, 168, 170 and a dichroic mirror 172 used in the excitation path but focusing lenses 174, 176 may be used just upstream of the first and second detectors 36, 162 in conjunction with the filters 158, 160 along the emission path in order to switch surfaces and achieve multiple color channels. Once again, this illustrated embodiment may also be extended to use any number of detectors to increase throughput and scanning efficiency.

Figure 22:
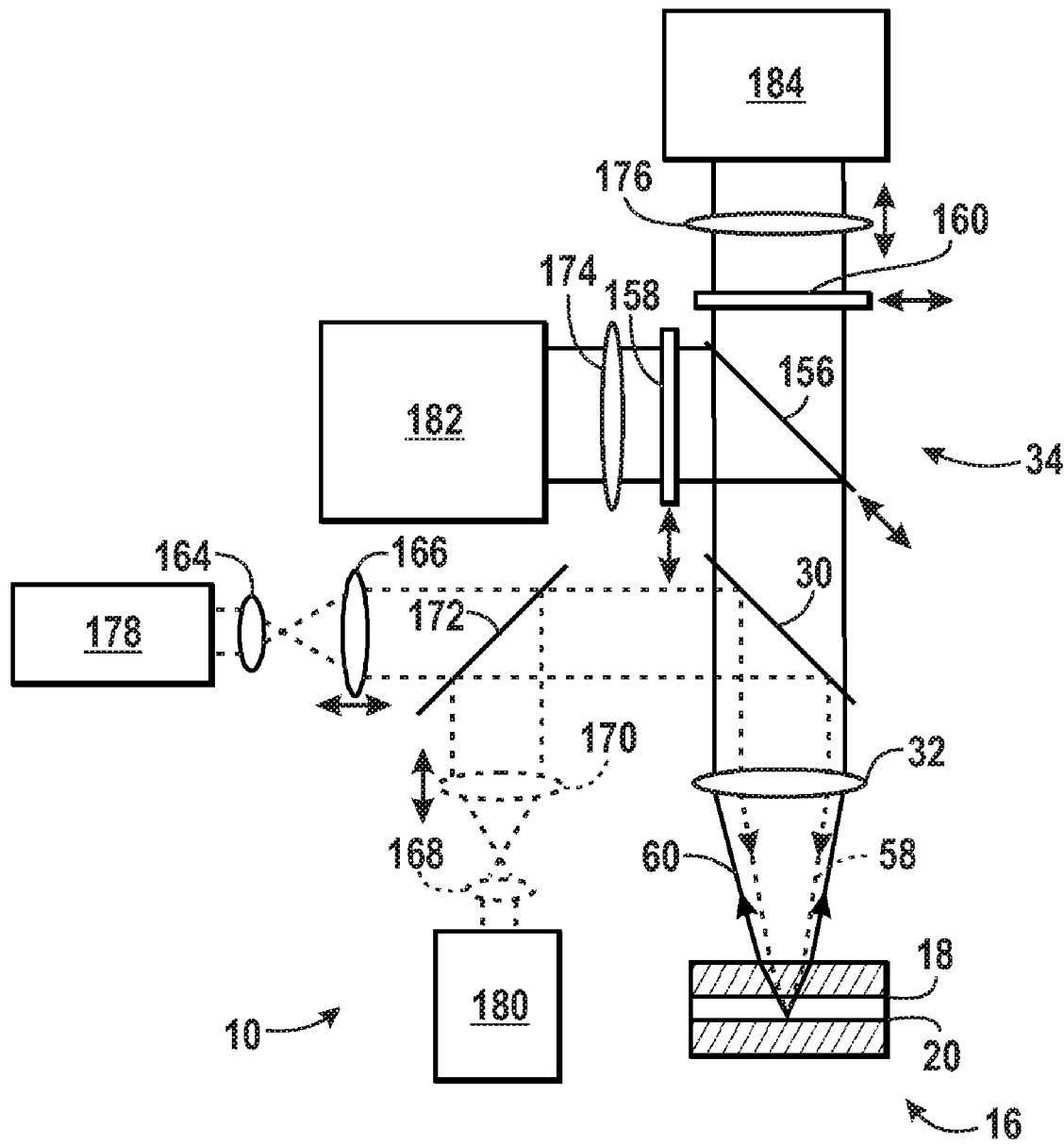
FIG. 22 is a diagrammatical view of a biological sample imaging system with multiple radiation sources and multiple detectors configured to simultaneously scan multiple surfaces of the support structure using focusing lenses along the excitation and emission paths in accordance with the present invention.

For instance, FIG. 22 illustrates an embodiment utilizing multiple radiation sources and multiple detectors which are capable of simultaneously outputting multiple channels with few moving parts. In the illustrated embodiment, radiation sources 22 and 24 have been replaced by radiation source groups 178 and 180 which are capable of outputting multiple radiation sources and varying wavelengths. In addition, detectors 36 and 38 have been replaced by detector groups 182 and 184 in the illustrated embodiment. These detector groups 182, 184 are similarly capable of detecting multiple color channels. This embodiment therefore illustrates the considerable adaptability of the present techniques to a range of configurations capable of imaging components on multiple surfaces of the support.

In the embodiments described above where scanning of the first and second surfaces 18, 20 of the support structure 16 may be performed simultaneously, focusing of the excitation radiation 58 source may be accomplished in several various ways. For instance, it may be possible to focus the excitation radiation 58 on one of the surfaces preferentially over the other surface. In fact, due to the nature of the configuration of the first surface 18 with respect to the second surface 20, it may be necessary to do so. However, alternate focusing techniques may be employed depending on the specific configuration of the support structure 16. Moreover, it may be advantageous in these various configurations to first image the upper surface (i.e., the surface closer to the radiation source) in order to reduce photobleaching of the components on that surface that could result from first imaging the lower surface (i.e., the surface farther from the radiation source). Such selection of which surface to image may apply both when the surfaces are imaged sequentially as well as when they are imaged simultaneously.

In addition, the embodiments disclosed above have illustrated an epifluorescent imaging scheme wherein the excitation radiation is directed toward the surfaces of the support structure 16 from a top side, and returned fluorescent radiation is received from the same side. However, the techniques of the present invention may also be extended to alternate arrangements. For instance, these techniques may also be employed in conjunction with TIR imaging whereby the surfaces of the support structure are irradiated from a lateral side with radiation directed at an incident angle within a range of critical angles so as to convey the excitation radiation within the support or into the support from a prism positioned adjacent to it. TIR techniques can be carried out as described, for example, in U.S. Patent Application Publication No. 2005/0057798, which is hereby incorporated by reference. Such techniques cause fluorescent emissions from the components that are conveyed outwardly for imaging, while the reflected excitation radiation exits via a side opposite from that through which it entered. Here again, biological components on the multiple surfaces may be imaged sequentially or simultaneously.

Figure 23:
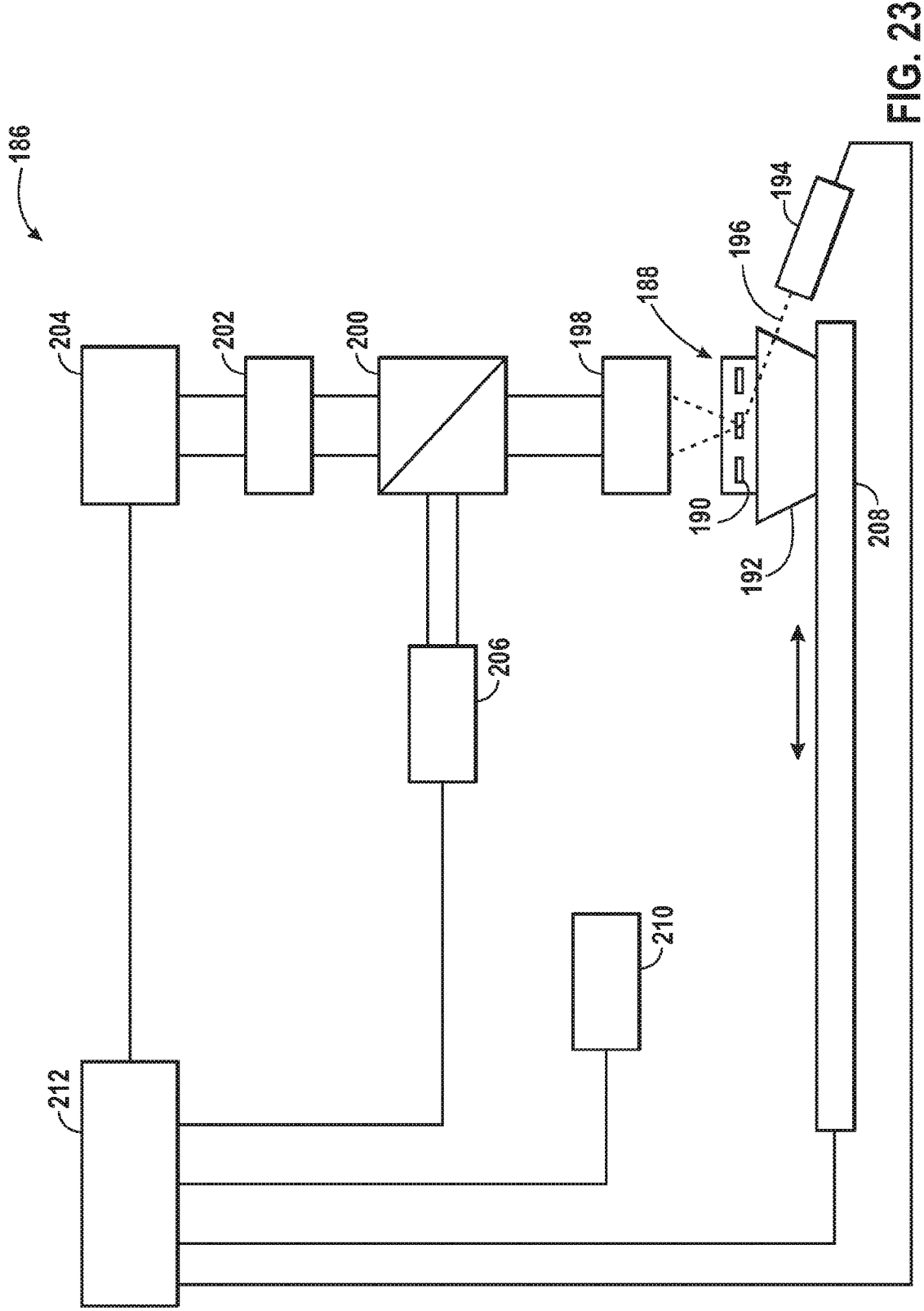
FIG. 23 is a diagrammatical overview for a TIR biological sample imaging system in accordance with the present invention.

For example, in FIG. 23, a TIR biological sample imaging system 186 is illustrated diagrammatically. A support structure 188 may be used which includes multiple flow lanes 190 containing biological components. For example, the support structure 188 may be a flow cell through which reagents, flushes, and other fluids may be introduced using the flow lanes 190 to contact emissive components attached to the surface of the flow cell. The support structure 188 may be supported by a prism 192. In the TIR biological sample imaging system 186, the radiation source 194 may output a radiation beam 196 through the prism 192 from a lateral side of the support structure 188. The radiation beam 196 may, for instance, be directed toward a bottom surface of one of the flow lanes 190 of the support structure 188, thereby exciting emissive components attached to the surface.

As discussed in further detail below, as long as the incident angle of the radiation beam 196 is within the range of critical angles (as described, for example, in US 2005/0057798), a portion of the radiation beam 196 will be reflected off the bottom surface whereas a separate fluorescent emission beam from surface-bound emissive components will be directed toward focusing optics 198. Typically, a well collimated radiation beam is used to prevent spread of angles within the beam, thereby preventing unwanted hindrance of total internal reflectance. The fluorescent emission beam may propagate back through the focusing optics 198, directing optics 200, and detection optics 202 which may direct the beam toward a detector 204. The focusing optics 198, directing optics 200, detection optics 202, and detector 204 may operate in much the same manner as with the epifluorescent techniques discussed above. In the TIR biological sample imaging system 186, the focusing light source 206 may be used as a separate light source from the radiation source 194 to focus the optics on a particular surface to be imaged. For instance, the focusing light source 206 may be directed to the directing optics 200 where it is redirected toward the focusing optics 198 which are used to focus the system on a particular surface of the support structure 188.

The TIR biological sample imaging system 186 may also include a translation system 208 for moving the support structure 188 and prism 192 in one or more dimensions. The translation system 208 may be used with focusing, redirecting the radiation source 194 to different areas of the support structure 188, as well as for moving the support structure 188 and prism 192 to a heating/cooling station 210. The heating/cooling station 210 may be used to heat and cool the support structure 188 before and after imaging. In addition, a control/processing system 212 may be used to control operation of the radiation source 194, the focusing light source 206, and the heating/cooling station 210, movement and focusing of the focusing optics 198, the translation system 208, and the detection optics 202, and acquisition and processing of signals from the detector 204.

Figure 24:
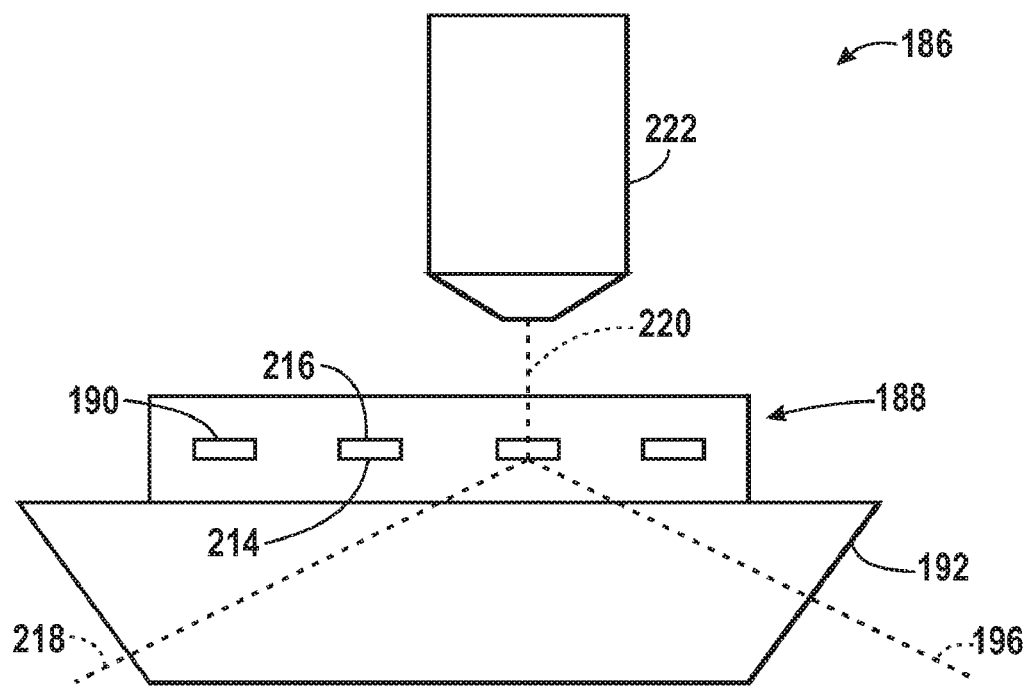
FIG. 24 is a sectional view of an exemplary support structure, prism, and lens objective for use with TIR imaging of a bottom surface of a flow lane in accordance with the present invention.

As discussed above, the TIR method of imaging may be used to direct the radiation beam 196 from a lateral side of the support structure 188, as illustrated in FIG. 24. Each flow lane 190 of the support structure 188 may include a bottom surface 214 and a top surface 216 and emissive components can optionally be attached to either or both surface. In the illustrated embodiment, the radiation beam 196 is directed toward a bottom surface 214 of one of the flow lanes 190 of the support structure 188. Part of the radiation beam 196 may be reflected off the bottom surface 214 of the flow lane 190, as depicted by reflected light beam 218. However, as long as the incident angle of the radiation beam 196 is within the range of critical angles, a separate fluorescent emission beam 220 may be emitted from emissive components toward the focusing optics 198 which in the illustrated embodiment is a lens objective 222. Indeed, directing the radiation beam 196 at a bottom surface 214 of a flow lane 190 of the support structure 188 is a typical implementation of the TIR imaging method. However, in doing so, imaging data which may be collected from a top surface 216 of a flow lane 190 of the support structure 188 may be overlooked.

Figure 25:
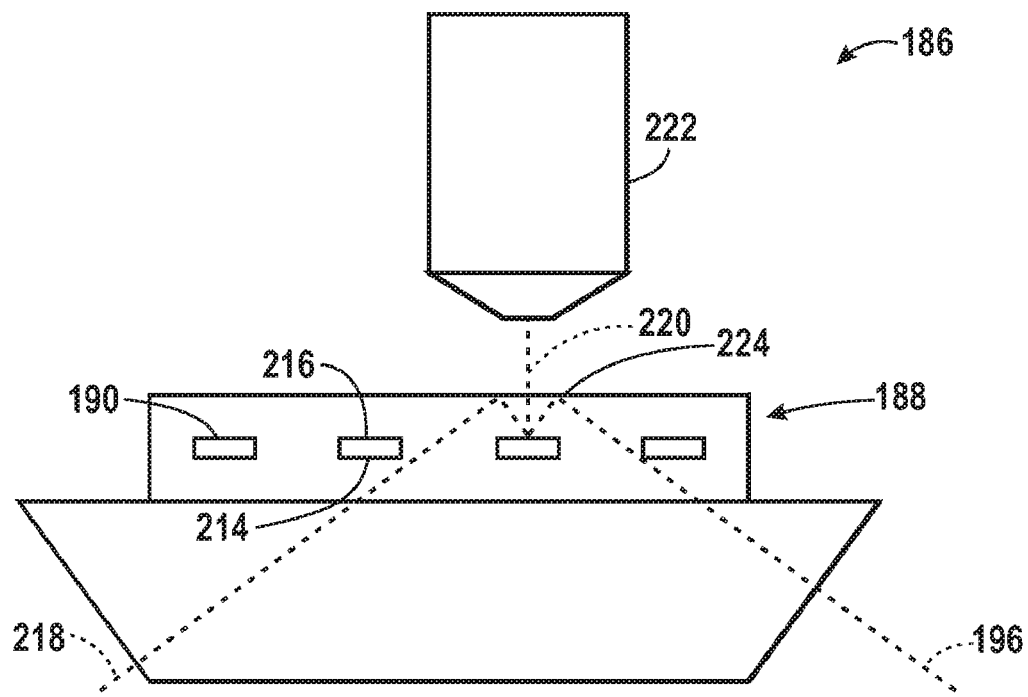
FIG. 25 is a sectional view of an exemplary support structure, prism, and lens objective for use with TIR imaging of a top surface of a flow lane in accordance with the present invention.

Therefore, the orientation of the radiation source 194 and/or the support structure 188 and prism 192 may be adjusted in order to allow the radiation beam 196 to not be directed at a bottom surface 214 of a flow lane 190 of the support structure 188, as illustrated in FIG. 25. In the illustrated embodiment, the radiation beam 196 is oriented so that the radiation beam 196 passes through the prism 192 and support structure 188 until contacting an air/glass interface 224 of the support structure 188 at which point the radiation beam 196 is redirected toward a top surface 216 of a flow lane 190 of the support structure 188. At this point, part of the radiation beam 196 may be reflected back toward another air/glass interface 224 of the support structure 188. However, a separate fluorescent emission beam 220 may be emitted from an emissive component on the top surface 216 toward the lens objective 222. Using this technique, top surfaces 216 of the flow lanes 190 of the support structure 188 may be imaged using TIR imaging methods. This, in effect, may allow for double the imaging data output for cluster based sequencing applications while keeping other variables, such as surface coating, cluster creation, and sequencing, the same.

In order to accomplish this TIR imaging of top surfaces 216 of the flow lanes 190 of the support structure 188, the radiation beam 196 reaches the air/glass interface 224 of the support structure 188 unperturbed. To do so, the radiation beam 196 does not first come into contact with emissive components in adjacent flow lanes 190. To do so, either the radiation beam 196 may be directed around the adjacent flow lanes 190 or the adjacent flow lanes 190 may be index matched with the support structure 188 material. In some embodiments, the flow lanes 190 may be spaced within the support structure 188, leaving sufficient room between the flow lanes 190 for the radiation beam 196 to pass. However, spacing the flow lanes 190 in this manner may ultimately reduce the amount of emissive components which may be imaged. Therefore, in other embodiments, it may be possible to accomplish the same effect by temporarily filling alternate flow lanes 190 with index matching fluid. Doing so may allow for easier direction of the radiation beam 196 toward a top surface 216 of a flow lane 190 of the support structure 188.

Figure 26:
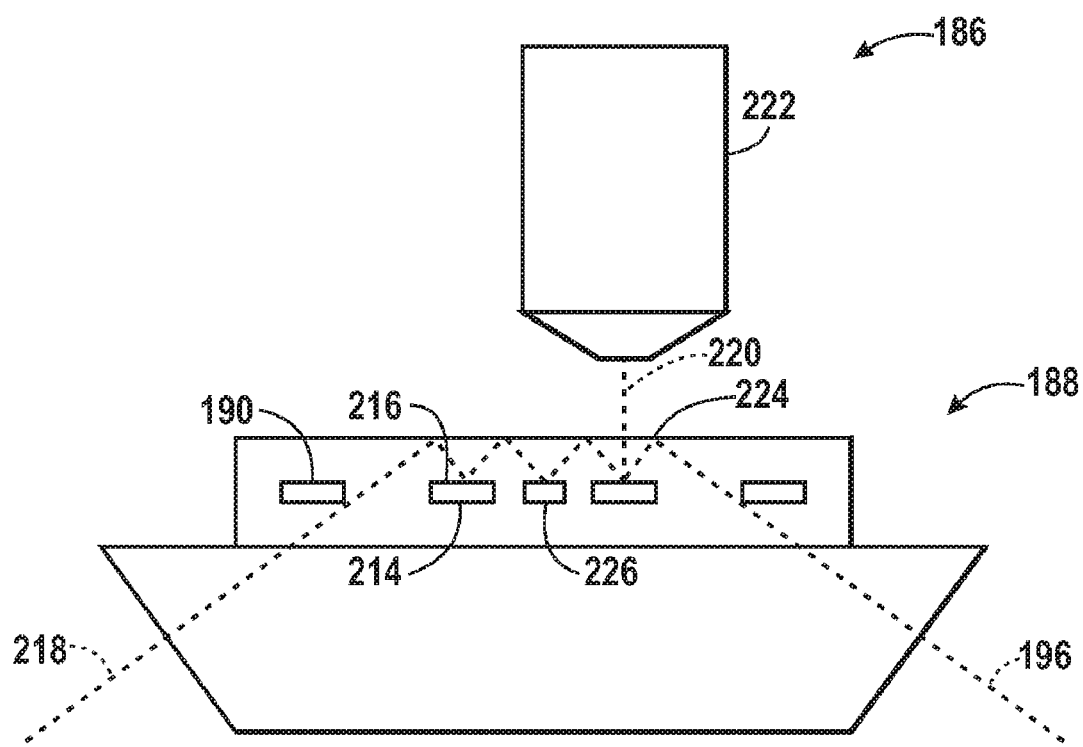
FIG. 26 is a sectional view of another exemplary support structure, prism, and lens objective for use with TIR imaging of a top surface of a flow lane in accordance with the present invention.

It may also be possible to direct the radiation beam 196 in such a way that it bounces off multiple top surfaces 216 of flow lanes 190 of the support structure 188, as illustrated in FIG. 26. In order to accomplish this, the spacing of the flow lanes 190 can be matched with the angle of radiation beam 196 such that the radiation beam 196 is able to pass by the flow lanes 190, such that it reaches the air/glass interface 224 of the support structure 188 unperturbed, while also being able to bounce back and forth between top surfaces 216 of flow lanes 190 and the air/glass interface 224 of the support structure 188. As described above, in certain embodiments, some of the flow lanes 190 may be filled with an index matching fluid, such that these index-matched flow lanes 190 effectively become "invisible" to the radiation beam 196. In other words, the radiation beam 196 may be allowed to pass through the index-matched flow lanes 190. By allowing the radiation beam 196 to pass through the index-matched flow lanes 190, the support structure 188 may be used in multiple configurations without the need of varying the spacing of the flow lanes 190.

In some embodiments, mirrors 226 or other suitable reflective material may be used within certain flow lanes 190, facilitating this multi-bounce technique. In any event, assuming N number of flow lanes 190, it may only be possible to image N-2 number of top surfaces 216 of the flow lanes 190 in this manner due to the fact that the outer flow lanes 190 on either side of the support structure 188 may not be accessible using these techniques. However, modification of the prism 192 and/or support structure 188 may allow for imaging of the top surfaces 216 of these outermost flow lanes 190. For instance, the support structure 188 may be designed to fit within the prism 192, allowing the radiation beam 196 to propagate into a lateral side of the support structure 188.

Figure 27:
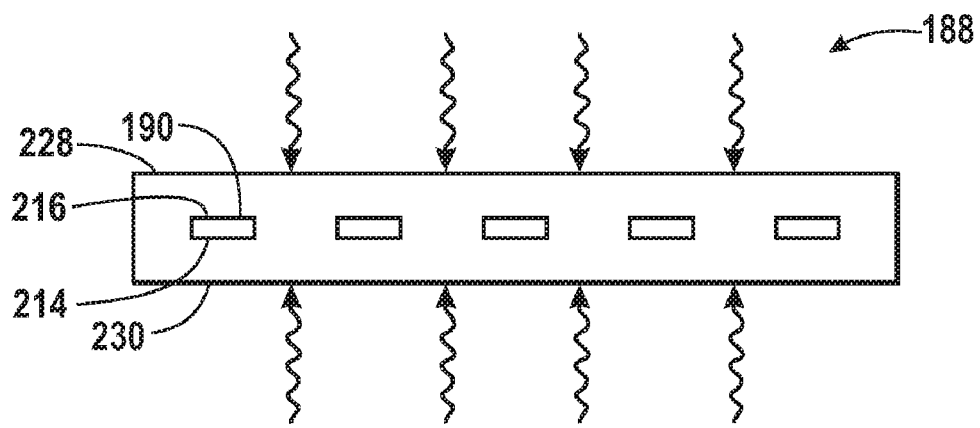
FIG. 27 is a sectional view of an exemplary support structure being heated on both top and bottom surfaces in accordance with the present invention.

In some embodiments, as discussed above briefly with respect to FIG. 23, the support structure 188 may be moved to a heating/cooling station 210, for example, by the action of the translation system 208. The heating/cooling station 210 may be configured to both heat and cool the support structure 188 before and after imaging. The heating/cooling station 210 may, in fact, be configured to heat and cool both a top surface 228 and a bottom surface 230 of the support structure 188, as illustrated in FIG. 27. Indeed, all surfaces of the support structure 188 may be heated or cooled at the heating/cooling station 210. In this manner, it may further be possible to heat and cool both the top surfaces 216 and bottom surfaces 214 of the flow lanes 190 of the support structure 188 by directly contacting one or more surfaces of the flow cell with a heating or cooling device. This, of course, may facilitate the development of biological components within the flow lanes 190 of the support structure 188 and, therefore, facilitate imaging. Although use of the heating/cooling station 210 has been presented herein with respect to the TIR imaging methods, the heating/cooling station 210 may also be used to heat and cool multiple sides of a support structure used in conjunction with the epifluorescent imaging methods discussed herein.

In particular embodiments, the current invention utilizes sequencing-by-synthesis (SBS). In SBS, four fluorescently labeled modified nucleotides are used to determine the sequence of nucleotides for nucleic acids present on the surface of a support structure such as a flow cell. Exemplary SBS systems and methods which can be utilized with the apparatus and methods set forth herein are described in U.S. Pat. No. 7,057,026; U.S. Patent Application Publication Nos. 2005/0100900, 2006/0188901, 2006/0240439, 2006/0281109, and 2007/0166705; and PCT Publication Nos. WO 05/065814, WO 06/064199, and WO 07/010251; each of which is incorporated herein by reference.

In particular uses of the apparatus and methods herein, flow cells containing arrayed nucleic acids are treated by several repeated cycles of an overall sequencing process. The nucleic acids are prepared such that they include an oligonucleotide primer adjacent to an unknown target sequence. To initiate the first SBS sequencing cycle, one or more differently labeled nucleotides and a DNA polymerase are flowed into the flow cell. Either a single nucleotide can be added at a time, or the nucleotides used in the sequencing procedure can be specially designed to possess a reversible termination property, thus allowing each cycle of the sequencing reaction to occur simultaneously in the presence of all four labeled nucleotides (A, C, T, G). Following nucleotide addition, the features on the surface can be imaged to determine the identity of the incorporated nucleotide (based on the labels on the nucleotides). Then, reagents can be added to the flow cell to remove the blocked 3' terminus (if appropriate) and to remove labels from each incorporated base. Such cycles are then repeated and the sequence of each cluster is read over the multiple chemistry cycles.

Other sequencing methods that use cyclic reactions wherein each cycle includes steps of delivering one or more reagents to nucleic acids on a surface and imaging the surface bound nucleic acids can also be used such as pyrosequencing and sequencing by ligation. Useful pyrosequencing reactions are described, for example, in U.S. Pat. No. 7,244,559 and U.S. Patent Application Publication No. 2005/0191698, each of which is incorporated herein by reference. Sequencing by ligation reactions are described, for example, in Shendure et al. *Science* 309:1728-1732 (2005); and U.S. Pat. Nos. 5,599,675 and 5,750,341, each of which is incorporated herein by reference.

The methods and apparatus described herein are also useful for detection of features occurring on surfaces used in genotyping assays, expression analyses and other assays known in the art such as those described in U.S. Patent Application Publication Nos. 2003/0108900, US 2003/0215821, and US 2005/0181394, each of which is incorporated herein by reference.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for imaging a biological sample, comprising:
   (a) detecting radiation emitted from a first emissive component of a biological sample disposed on a first surface of a flow cell using a detector, wherein the flow cell is mounted on an imaging station;
   (b) inserting corrective optics between the detector and the flow cell;
   (c) detecting radiation emitted from a second emissive component of a biological sample disposed on a second surface of the flow cell using the detector and the corrective optics, wherein the first and second surfaces are in an arrangement whereby one of the surfaces is disposed between the detector and the other surface, wherein the corrective optics reduce aberration of detection at one of the surfaces due to the arrangement; and
   (d) repeating steps (a)-(c) while maintaining the flow cell on the imaging station.

2. The method of claim 1, wherein the first surface is disposed between the detector and the second surface.

3. The method of claim 2, wherein a fluid is present between the two surfaces and the corrective optics reduce aberration due to the fluid.

4. The method of claim 3, wherein the detector is initially configured for diffraction-limited detection on the second surface and the corrective optics are configured for diffraction-limited detection on the first surface.

5. The method of claim 3, wherein the aberration comprises spherical aberration.

6. The method of claim 1, wherein the first surface is disposed between a source of radiation and the second surface.

7. The method of claim 1, wherein step (b) comprises inserting a corrective device between an objective and the flow cell, wherein the objective is disposed between the detector and the flow cell.

8. The method of claim 1, wherein step (b) comprises inserting a corrective lens between the detector and an objective, wherein the objective is disposed between the detector and the flow cell.

9. The method of claim 1, wherein step (a) and (c) comprise obtaining an image of the surfaces.

10. The method of claim 1, wherein steps (a) and (c) comprise focusing a line of radiation to an area on the first or second surface comprising the first or second emissive component.

11. The method of claim 1, wherein the emitted radiation is detected using epifluorescent excitation.

12. The method of claim 1, wherein an excitation radiation is directed towards the first and second surfaces by total internal reflection excitation.

13. The method of claim 12, wherein the excitation radiation and flow cell are configured to produce a total internal reflectance bounce that excites the first surface and the second surface.

14. The method of claim 1, wherein the first and second emissive components comprise fluorescently tagged nucleic acids of a nucleic acid sample.

15. The method of claim 1, wherein the first and second emissive components comprise separate features in arrays of features on the first and second surfaces, respectively.

16. The method of claim 15, wherein the separate features each comprise a population of identical molecules.

17. The method of claim 1, wherein a chromatic shift curve for the radiation detected in step (a) is the same as a chromatic shift curve for the radiation detected in step (b).

18. The method of claim 1, wherein a field curvature for detection in step (a) is the same as a field curvature for detection in step (b).

19. The method of claim 1, wherein a field distortion for detection in step (a) is the same as a field distortion for detection in step (b).

20. An imaging system for detecting radiation on a multi-surface flow cell, comprising:
   a multi-surface flow cell having first and second emissive components of a biological sample disposed on respective first and second surfaces of the flow cell;
   an optical train comprising an objective, imaging optics configured to focus the optical train on the first emissive component via the objective, and corrective optics configured to focus the optical train on the second emissive component and configured to reduce aberration of detection at the first or second emissive component;
   a radiation source configured to direct excitation radiation towards the first and second emissive components;
   detection optics configured to capture emitted radiation returned from the first and second emissive components via the optical train; and
   a detector for detecting the captured radiation.

21. The imaging system of claim 20, wherein components of the corrective optics that are configured to focus the optical train on the second emissive component are separate from components of the corrective optics that are configured to reduce aberration of detection at the first or second emissive component.

22. The imaging system of claim 20, wherein the corrective optics comprise a corrective device configured to be inserted between the objective and the flow cell.

23. The imaging system of claim 20, wherein the corrective optics comprise a corrective lens configured to be inserted between the detector and the objective.

24. The imaging system of claim 20, wherein the radiation source is configured to direct the excitation radiation toward the first and second emissive components at several different wavelengths, and the detection optics and detector are configured to capture and detect the emitted radiation returned in response to each wavelength.

25. The imaging system of claim 20, wherein the flow cell includes a fluid in an interior volume and in contact with the biological samples.

26. The imaging system of claim 20, wherein the first and second emissive components comprise fluorescently tagged nucleic acids from a nucleic acid sample.

27. The imaging system of claim 20, wherein the first surface is disposed between the radiation source and the second surface.

* * * * *